(12) United States Patent
Salganicoff

(10) Patent No.: US 7,460,130 B2
(45) Date of Patent: Dec. 2, 2008

(54) METHOD AND SYSTEM FOR GENERATION, STORAGE AND DISTRIBUTION OF OMNI-DIRECTIONAL OBJECT VIEWS

(75) Inventor: Marcos Salganicoff, Philadelphia, PA (US)

(73) Assignee: Advantage 3D LLC, Philadelphia, PA (US)

( * ) Notice: Subject to any disclaimer, the term of this patent is extended or adjusted under 35 U.S.C. 154(b) by 0 days.

(21) Appl. No.: 10/380,720

(22) PCT Filed: Sep. 21, 2001

(86) PCT No.: PCT/US01/29640

§ 371 (c)(1),
(2), (4) Date: Mar. 18, 2003

(87) PCT Pub. No.: WO02/27659

PCT Pub. Date: Apr. 4, 2002

(65) Prior Publication Data

US 2004/0034295 A1     Feb. 19, 2004

Related U.S. Application Data

(60) Provisional application No. 60/235,319, filed on Sep. 26, 2000, provisional application No. 60/266,099, filed on Feb. 5, 2001.

(51) Int. Cl.
*G06F 9/00* (2006.01)
*G06F 3/14* (2006.01)
*G06K 9/00* (2006.01)
*H04N 7/18* (2006.01)

(52) U.S. Cl. ........................ 345/590; 345/630; 345/561; 345/606; 345/640; 348/490; 348/583; 358/537; 358/540; 715/723; 382/107; 382/723

(58) Field of Classification Search ......... 345/606–630, 345/640, 427–428, 581–597, 639, 643, 690–699, 345/561, 555–556; 348/582–586, 590–595, 348/508, 573, 490, 439; 358/444, 517, 525, 358/537–540; 382/107, 236, 168–170
See application file for complete search history.

(56) References Cited

U.S. PATENT DOCUMENTS 5,680,487 A * 10/1997 Markandey ................. 382/291
5,969,755 A     10/1999 Courtney
6,122,403 A     9/2000 Rhoads (Continued)

*Primary Examiner*—Wesner Sajous
(74) *Attorney, Agent, or Firm*—Synnestvedt & Lechner LLP

(57) ABSTRACT

Image acquisition refers to the taking of digital images of multiple views of the object of interest. In the processing step, the constituent images collected in the image acquisition step are selected and further processed to form a multimedia sequence which allows for the interactive view of the object. Furthermore, during the Processing phase, the entire multimedia sequence is compressed and digitally signed to authorize it viewing. In the Storage and Caching Step, the resulting multimedia sequence is sent to a storage servers. In the Transmission and viewing step, a Viewer (individual) may request a particular multi-media sequence, for example, by selecting a particular hyperlink within a browser, which initiates the downloading, checking of authorization to view, decompression and interactive rendering of the multi-media sequence on the end-users terminal, which could be any one of a variety of devices, including a desktop PC, or a hand-held device.

12 Claims, 36 Drawing Sheets

U.S. PATENT DOCUMENTS

| | | |
|---|---|---|
| 6,128,046 A | 10/2000 | Totsuka et al. |
| 6,175,343 B1 | 1/2001 | Mitchell et al. |
| 6,269,195 B1 * | 7/2001 | Gonsalves et al. .......... 382/284 |
| 6,335,977 B1 * | 1/2002 | Kage .......................... 382/107 |
| 6,429,892 B1 | 8/2002 | Parker |
| 2002/0025066 A1 * | 2/2002 | Pettigrew .................... 382/162 |
| 2002/0037103 A1 * | 3/2002 | Hong et al. ................. 382/173 |
| 2007/0160289 A1 * | 7/2007 | Lipton et al. ................ 382/173 |

* cited by examiner

Kiosk

Slider Image

```
<HTML>
<SCRIPT LANGUAGE="JavaScript">
<!--
cellobj1 = new Image;
cellobj1.src = "./view1.jpg";
cellobj2 = new Image;
cellobj2.src = "./view2.jpg";
cellobj3 = new Image;
cellobj3.src = "./view3.jpg";
cellobj4 = new Image;
cellobj4.src = "./view4.jpg";
sliderobj1 = new Image;
sliderobj1.src = "./slider1.gif";
sliderobj2 = new Image;
sliderobj2.src = "./slider2.gif";
sliderobj3 = new Image;
sliderobj3.src = "./slider3.gif";
sliderobj4 = new Image;
sliderobj4.src = "./slide4.gif";
function SelectImage(imgID,imgID1,imgName,imgName1) {
        document.images[imgID].src = eval(imgName + ".src")
        document.images[imgID1].src = eval(imgName1 + ".src")
        }
// -->
</SCRIPT>
```

Figure 52

```
<center>
  <map name="mymap">
  <area name="Area1" coords="0,0,102,54"
  href="#"
  onmouseover="selimage('View','Slider','cellobj1','sliderobj1')">
  <area name="Area2" coords="102,0,195,54"
  href="#"
  onmouseover="selimage('View','Slider','cellobj2','sliderobj2')">
  <area name="Area3" coords="195,0,288,54"
  href="#"
  onmouseover="selimage('View','Slider','cellobj3','sliderobj3')">
  <area name="Area4" coords="288,0,396,54"
  href="#"
  onmouseover="selimage('View','Slider','cellobj4','sliderobj4')">
  </MAP>
<img src="./view1.jpg" border="0" name="View">
<img src="slider1.gif" border="0" name="Slider" usemap="#mymap">
</center>
</BODY>
</HTML>
```

Figure 52 Continued

METHOD AND SYSTEM FOR GENERATION, STORAGE AND DISTRIBUTION OF OMNI-DIRECTIONAL OBJECT VIEWS

BACKGROUND OF THE INVENTION

1. Field of the Invention

The present invention relates generally to imaging and more specifically to imaging of objects.

2. Brief Description of the Prior Art

A common obstacle to the sale of items on the Internet is that it is difficult for consumers to gain an understanding of the three-dimensional characteristics of an item being contemplated for purchase. In the conventional retail store environment, the consumer often has the opportunity to look at an item of interest from multiple directions and distances. This in-person experience allows the consumer to understand and appreciate the physical shape and detail of the object more closely and to be assured that the item they are purchasing meets their expectations in terms of quality, desired feature set and characteristics. On the Internet, achieving a similar level of interactive product inspection and evaluation by a consumer is much more difficult, since the browsing experience of most Internet consumers is primarily a two dimensional one e.g. looking at pictures or reading text descriptions of items. While this gives a reasonable representation of the object, more complete interaction which rivals that available in a conventional retail environment can be desirable. Such an experience would reduce the barriers to purchasing over the Internet that might have resulted due to the user having an incomplete picture which is limited to the 2-D static photographs, non-interactive video, illustrations and textual descriptions of the item being contemplated for purchase. A system and method which would allow for a multi-view interactive experience of items would be desirable to consumers and vendors alike.

Images are useful in depicting the attributes of scenes, people and objects. However, the advent of digitized imagery has demonstrated that the image can become an active object that can be manipulated digitally via computer processing. Images can also become interactive entities, where clicking on different portions of an image can yield different processing outcomes which could come from a variety of multimedia sources, such as sounds, animations, other images, text, etc. For example, image maps are used often within the wide world web allow for a large of amount of information to be displayed in an intuitive graphical fashion to a user allowing for "direct manipulation" GUIs, By clicking within different portions of the image, different outcomes can be triggered, such as loading of web pages that are linked to those portions of the images, or "roll overs" which dynamically display additional text describing a button which may be selected. For example, a 3D effect can be achieved by acquiring a set of images of a rotating object in sequence in then allow for the smooth sequential selection of those images by the use of a GUI element such as a slider, thus giving the appearance of 3D rotational object motion. The images may be from real scenes, or synthetically generated using computer graphics techniques. This multimedia program may be in the form a browser embedded application or "Applet" as depicted in FIG. 1.

Additionally, besides linking to other images or web pages with multimedia content, different input actions to a multimedia programs (e.g. an internet browser) can cause the selection of different images, such as causing the display of magnified portions around the area clicked and so forth.

Additionally, with the advent of digital image processing programs aimed at the digital manipulation and enhancement of digitized images, it has become possible for multimedia authors to easily and intuitively build image-based interactive programs which can be run within any web browser. For example, multimedia authoring programs which run on the PC, such as Adobe LiveMotion or MacroMedia Director™ allow developers to create content for CDs, DVDs and the web.

The system described here enhances and extends existing systems and processes for digital image editing and multimedia authoring in a number of novel ways which are described below.

It is presently difficult to generate interactive multiple view images of objects for a number of reasons. Stand-alone Software applications for creation of interactive object viewing are complex it install and use, and are expensive to purchase. For example, applications such as MGI Photo Vista 3D Objects, VR Objectworx and Quicktime VR Authoring Studio are complex to install, and difficult to master for a non-technical audience. We present an self-installing application which runs inside a web-browser, and is easy to use, even for the technically untrained.

Another drawback of existing programs for the creation of interactive multiple view images has been the high up front cost of purchasing these applications, since they are sold on a licensing basis which presumes an unlimited number of images may be created for each granted license. We present a methods and architectures which permit the software to be freely distributed and licensed on a pay-per-use basis using cryptographic techniques to enforce the terms of the licensing.

An additional impediment faced by the prior art in interactive image generation is that expensive special purpose rotating stages must be purchased to rotate the object to be photographed. This additional cost is such that many individuals that might desire to generate interactive images are currently prevented from doing so by the high costs and complexity of purchasing and installing the electromechanical systems required to acquire such images. We provide several ways which eliminate these barriers by providing a software only means to acquire said images, by enabling the use of extremely low cost spring wound rotating stages, and by providing a self-service kiosk with all of the necessary hardware elements to carry out the image acquisition and processing necessary to achieve the generation of the interactive images.

In the current state of the art of multi-media, the notion of the multi-media player refers to an application program which can interpret media objects and multi-media programs in order to present a multi-media presentation to an end-user. The player can operate in an open loop fashion, deterministically presenting media objects without end-user intervention, or may be interactive, where the presentation sequence of the media objects may be controlled by certain user inputs.

In general, most multi-media systems, such as MacroMedia's Flash system, require a native multi-media player plug-in, which interprets files in Flash Format that contain the specific multi-media instructions and objects that will carry out the presentation. The Flash player is written in the native instruction set of the computer that is rendering the multimedia presentation. Since the processor cannot natively interpret the multi-media sequence, this creates the pre-requisite that the user have installed the corresponding media player on their PC in order to be able to play the media sequence. The downloading and installation of the media player can impose an inconvenience on the end-user, since the media player can be large and take a long time to download, and installation processes for media players can be error prone. It is therefore desirable to avoid this step. We describe a solution that uses a very small special purpose media player for our multi-media sequences which downloads in an almost instantaneous manner and is written in the Java programming language bytecode. Since the majority of Web browsers come with the Java bytecode interpreter pre-installed, the end-user can enjoy the multi-media sequences while avoiding the download of a full media player. The Java™ programming language provides a basis for a predictable run-time environment (Virtual Machine) for programs which operate on computer having differing processor instruction sets and operating systems. A number of major internet browsing programs provide a Java run-time environment which allows for programs compiled into Java byte code to execute within what is commonly known as an applet. An applet is a small program which runs within the context of a larger application such as a web browser and can execute inside of a standard web page as depicted in FIG. 1. The use of the Java Run Time eliminates the need for the installation of a specialized plug-in program to allow for the extension of the capabilities of the web browser, such as for, example, the MacroMedia Flash Player Plug-in. Instead, an applet written in the Java language and compiled into byte code may be used to add new programmatic feature (such as multimedia capabilities) to a browser. Other languages such as Microsoft's C# may serve as well for the implementation, replacing Java. Alternatively, Javascript may be used to animate the 3D sequences and provide interactive user input and reactivity if desired.

SUMMARY OF THE INVENTION

In one embodiment, the main steps in the operation of the system along with the associated hardware system components are indicated in FIG. 2.

The system processing flow can be broken into four main phases:
1. Image Acquisition
2. Processing
3. Storage
4. Transmission and Viewing The key hardware elements for realization of the system are:
1. Digital Photographic or Video Camera
2. Personal Computer (PC)
3. Application Host Server
4. Storage and Caching Servers
5. Viewing PCs Image acquisition refers to the taking of digital images of multiple views of the object of interest. In the processing step, the constituent images collected in the image acquisition step are selected and further processed to form a multimedia sequence which allows for the interactive view of the object. Furthermore, during the Processing phase, the entire multi-media sequence is compressed and digitally signed to authorize it viewing. In the Storage and Caching Step, the resulting multimedia sequence is sent to a storage servers. In the Transmission and viewing step, a Viewer (individual) may request a particular multi-media sequence, for example, by selecting a particular hyperlink within a browser, which initiates the downloading, checking of authorization to view, decompression and interactive rendering of the multi-media sequence on the end-users terminal, which could be any one of a variety of devices, including a desktop PC, or a hand-held device.

In the image acquisition step, image acquisition can be done by a variety of means, three of which are illustrated in the FIG. 2. For example, using a hand held CAMERA, VIDEO & PC, and hold the object of interest in a fixed position the user may circle the object and take a number of images which capture different aspects (directional views) of the object (See FIG. 3). These images are temporarily stored in the memory of the digital camera. Alternatively, by using a camera, such as a camera or video recorder, as depicted in STABILIZED CAMERA, AND/OR VIDEO, AND/OR ROTATING STAGE and PC, and placing the object on the rotating stage, and taking images at differing time intervals as the object rotates, a sequence of different aspects of the object can be captured. The camera may be stabilized either electronically, or by use of a tripod. Alternatively, the object can be manually rotated through a number of positions, and images acquired at the different object positions. In another image acquisition embodiment, a public situated SELF-CONTAINED ROTATING STAGE KIOSK containing, an illumination system, camera and rotating stage, can be used as a vending system, into which the object of interest is placed, and the kiosk automatically takes a series of images.

In the Processing Step, the images captured in the previous step are processed using a Processing application. The processing application permits all of the captured images illustrating the differing aspects of the object to be viewed, selected and aligned and then composed into an interactive multi-media sequence. This application may run stand-alone on the PC, in a shared mode, between a host computer and the users PC, or completely on the host, with the users PC acting as a thin client (see FIG. 4 and FIG. 5). The application provides a means for the building and preview of the finished sequence. Once the author is satisfied with the results of the sequence, the sequence is then compressed, encapsulated and authorized for distribution by the use of an authorizing digital signature.

In the storage step, the resulting sequence can be stored on a storage and distribution server which serves as a repository for the access of the finished multi-media sequences by the viewing public. The storage repository may be mirrored and distributed via a number of well known web caching mechanisms to improve the access time for the viewing public and distribute the load to the server Finally, in the Transmission and Viewing Step, member of the viewing public request specific multi-media sequences and view applet (see FIG. 1), for example, by selecting specific hyperlinks embedded within HTML, which triggers the transmission of the multi-media sequence to the viewing individuals terminal (whether a PC or handheld) where the sequence is authorized by checking of the digital signature decompressed and made available for interactive viewing.

BRIEF DESCRIPTION OF THE DRAWINGS

FIG. 52 is a listing of a Javascript program which realizes the multi-media image sequence presentation.

DETAILED DESCRIPTION OF THE INVENTION

Figure 1:
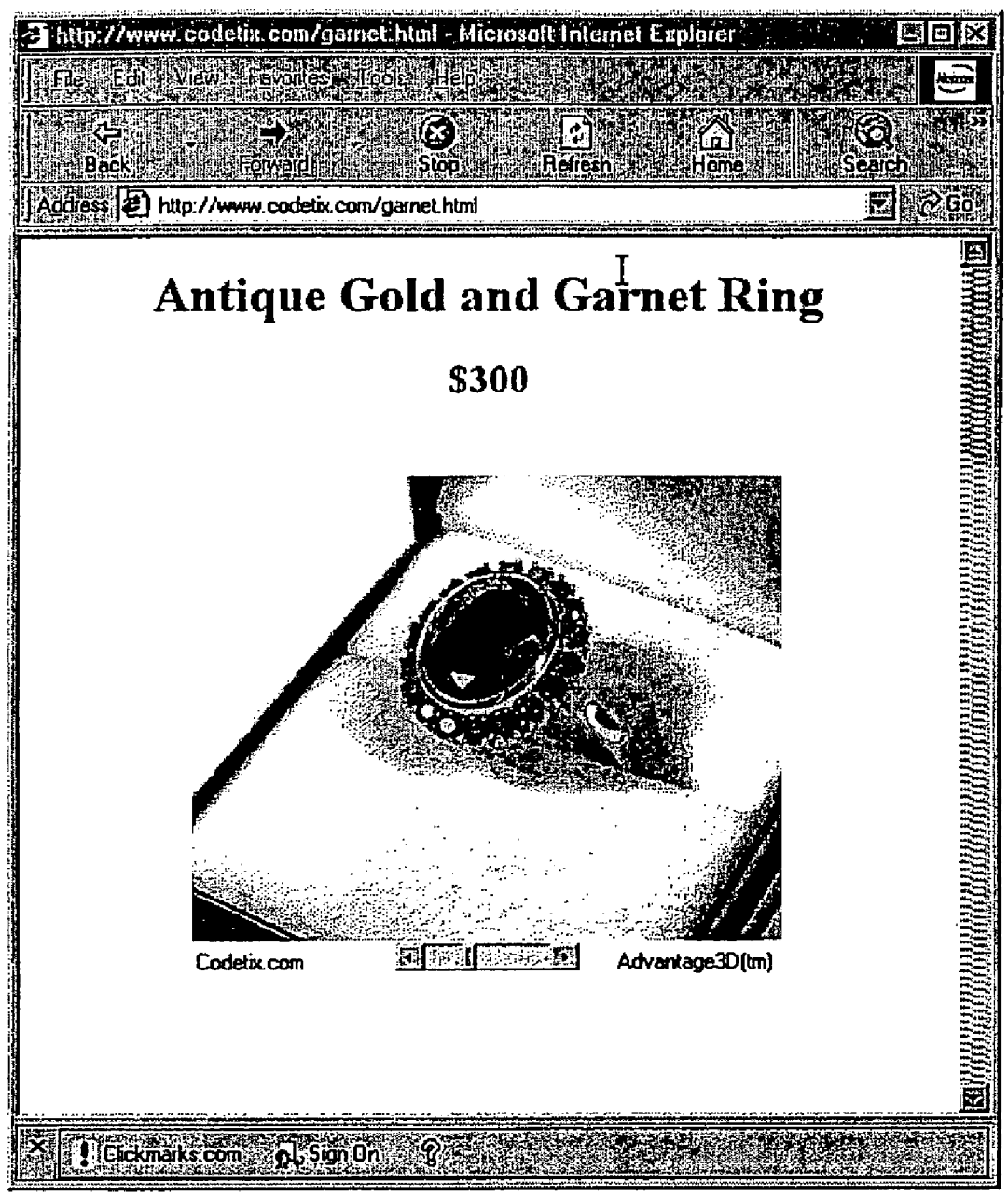
FIG. 1: Illustrates the Java Viewing Applet Embedded in a Browser Window

Referring now to the drawings in detail, a system in accordance with an embodiment of the invention includes a processing flow that can be broken into the following four main phases, which are described in more detail herein:

1. Image Acquisition
2. Processing
3. Storage
4. Transmission and Viewing

Picture Acquisition

In the image acquisition step, the constituent set of images making up the multi-media sequence are taken. This can be accomplished using a variety of different means, including the use of a Hand Rotated Object or Camera, Rotating Stage, or Self Contained View Acquisition Kiosk. These techniques are described in more detail below.

Hand Rotated Object or Camera

Figure 3:
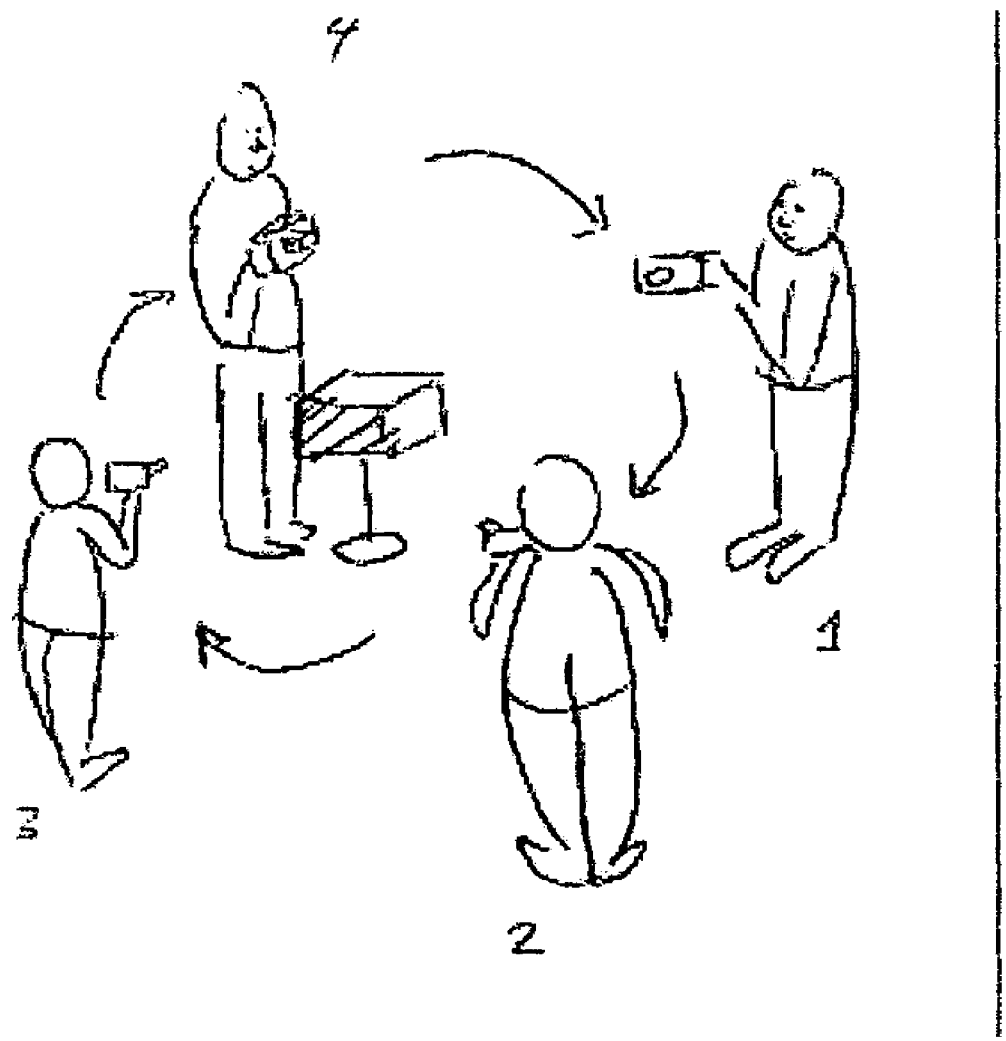
FIG. 3: Illustrates the process of acquisition of images around the object of interest using an image acquisition device.

In this mode a set of pictures are taken in one of two modes using a hand-held camera, either video or still. In the first mode, the object is held fixed and the camera is moved around the object while a sequence of images is taken, all the while keeping the object centered manually in the camera viewfinder apparatus. Alternatively, the handheld camera may be held approximately stationary and the object rotated in place by hand. At each new object rotational position, a new exposure is taken. This is illustrated in FIG. 3. Here positions 1 through 4 illustrate examples of different directions and ranges from which the images may be acquired using an image acquisition device.

Rotating Stage

Figure 6:
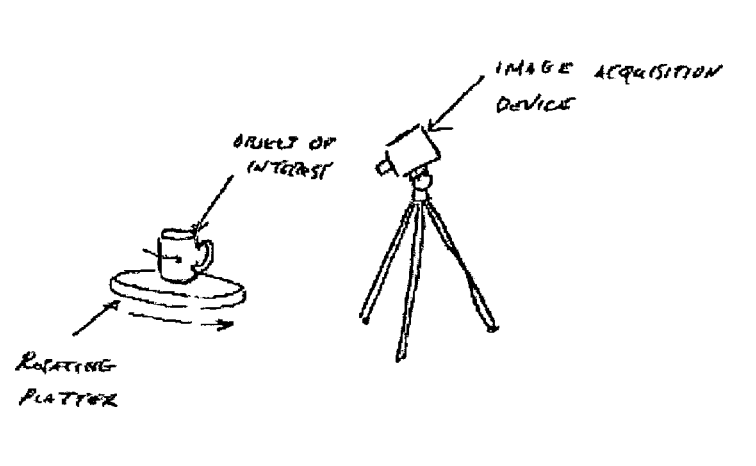
FIG. 6: Illustrates the image acquisition system for the camera, tripod and rotating platter.

A problem faced by individuals desiring to acquire 3-D interactive images is the expense of hardware and software need to acquire high-quality rotational interactive sequences of objects with the background suppressed and or composited. An alternative cost-effective procedure for achieving high quality object sequences is to use a slow-speed rotational table along with a time-lapse mode with a conventional digital camera. In the preferred embodiment a low cost spring wound rotational mechanism can be used, although dc and ac variable speed electrical motors can also be used. The acquisition setup is illustrated in FIG. 6, which has the image acquisition device, which can acquire and store the images, the rotating platter, which holds and rotates the object, and the tripod, which holds the camera steady between frame acquisitions.

In this mode, the object is placed on a rotating stage. The stage mechanism may be manually actuated, electrically actuated via an open or closed loop means, or spring actuated via wind-up. The stage is set to rotate while the camera is held fixed, either manually, or via tripod and a succession of exposures are taken at specific time or angle intervals. If closed loop control of the rotating stage is possible, then the rotating stage may be commanded to specific positions by the PC, and exposures taken upon completion of the motion. If the platform is moving in open loop fashion, and the platform rotational velocity in degrees/second is known, then the camera may be programming to automatically gather exposure at a given time interval that yield a given change in table rotational angle between exposure points.

The following procedure is used while holding the ambient scene lighting and camera exposure approximately constant between image acquisitions:

1. (Optional if "Automatic Masking via Background subtraction later described herein is used) The rotating stage and background are photographed without the desired object to yield a digital image($P_0$).

2. The desired foreground object is put on top of the slowly rotating turntable.

3. A sequence of images are taken in time lapse mode.

If shots are desired every n degrees of product rotation, then the timing interval between shots is set to n/(table rots/minute*360d/rot*1 minute/60 sec)=n/(degrees/sec) The total number of shots to be taken is N=int(360/n shots). ($P_1 \ldots P_N$)

The slow speed rotational table and editing/authoring applications may be "shrink wrapped" together to provide a complete 3D image acquisition solution to end-users which may be combined with the cryptographic based licensing techniques described in this document, or if desired, other well known license management technique may be used as well giving a simple and low cost solution for those desiring a low cost and convenient method for forming interactive image sequences with 3D characteristics in particular.

Self Contained View Acquisition System Kiosk

Some individuals may not wish to purchase and install the required elements for image acquisition, as described herein for reasons of convenience and expense. It is desirable to offer a vending system, which incorporates the necessary elements for carrying out the image acquisition in a simple self-service manner. Such a device can put in convenient public locations such as retail stores that would permit the displayer to avail himself of the scanning and posting capabilities of the machine by bringing the object of interest with him to that location. The automatic capabilities of the machine include the process of automatically acquiring, processing and publishing the omni-directional and distance views.

Figure 2:
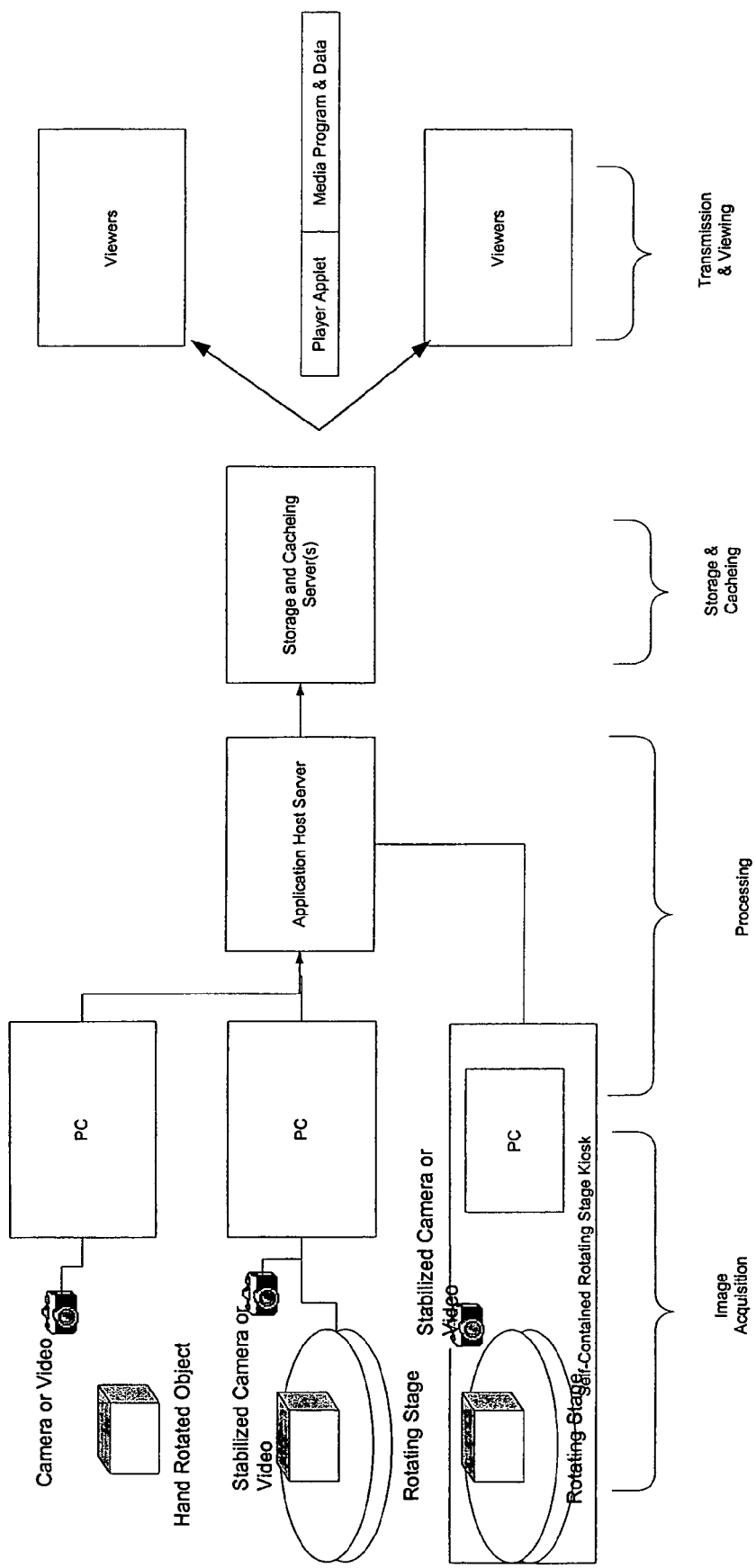
FIG. 2: Is an overview of the System for Generation, Storage and Distribution of Omni-directional Object Views.

A Self Contained View Acquisition System Kiosk (See FIG. 7) whose preferred embodiment is described in herein is connected to the Host Application Server of FIG. 2 which has the function of storing and sending the application Program to the PC at the request of the PC. In the first step, the object of interest can be placed on a computer controlled turntable (See FIG. 8) and camera pointing system with computer controlled adjustable camera parameters such as zoom, focus and pantilt and the turntable commanded to rotate to a succession of rotational angles, for each of which a digital image is acquired.

Once the views are acquired and temporarily stored on the PC, they can be adjusted and formatted into a media object using the Processing Application using any one of a number of different formats which are suitable for the economical storage and transmission of image sequences. A description of potential encodings is described later.

These view sequence files are transmitted and arrive at the Host Application Server where they are indexed and stored in the Storage and Caching Server(s) for future retrieval. A view sequence is cataloged by unique identifier which allow for the particular view sequence to be retrieved and viewed subsequently from the database within the Storing and Caching Server.

Embodiment for Self Contained Scanner

Figure 7:
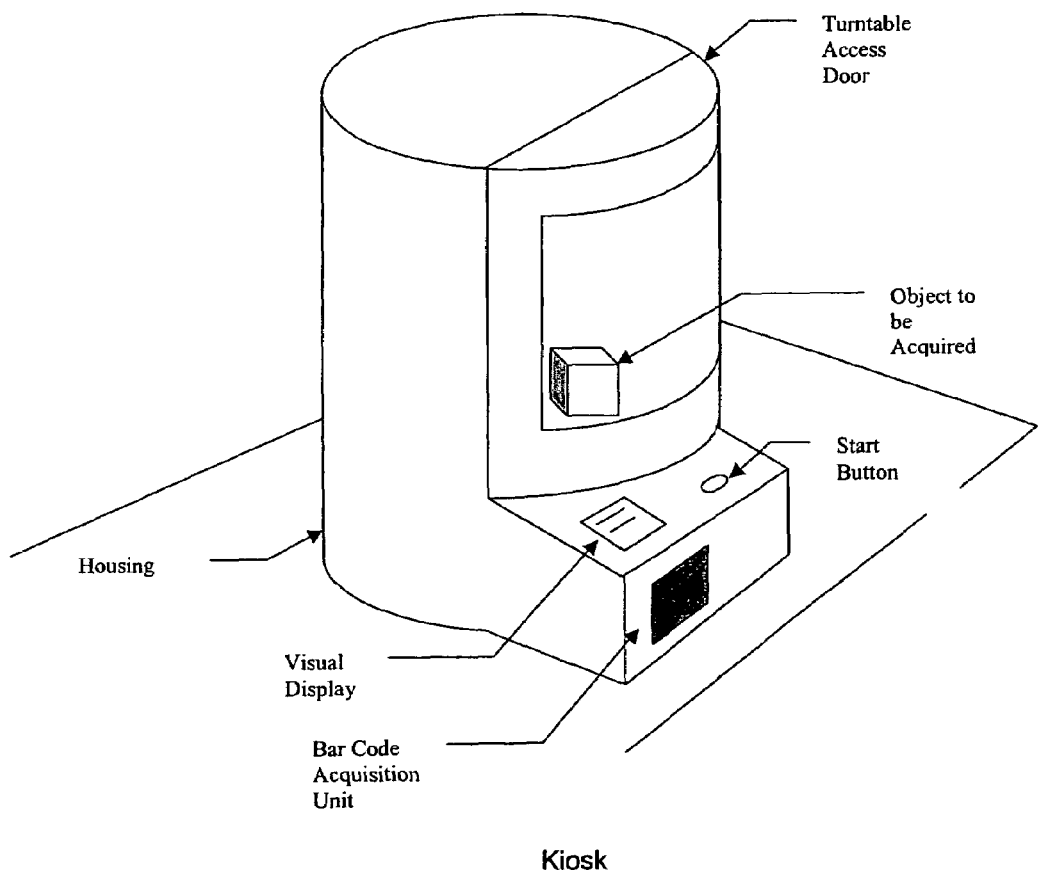
FIG. 7: Illustrates the Self Contained View Acquisition System Kiosk

It important for the displayer of goods to be able to easily and rapidly generate the omni-directional and omni-distance views of the object. The displayer of goods on the internet should be able to easily and conveniently generate omni-view sequences of objects and publish and link them. In a preferred embodiment, a kiosk such as illustrated in FIG. 7 can be used in a self-service fashion. The unit, which is countertop mounted, has a turntable access door which can swing open and the user can place the object to be acquired inside of the housing and close the door. The user then places the printed bar code label in front of the bar code acquisition unit which captures the unique object identifier. The user then may use the touch screen on the visual display to activate the collection of the view sequence. Once the view sequence collection is complete, the user may interactively preview the scan using the visual display.

Kinematic Configurations for Self-Contained Scanner

Figure 8:
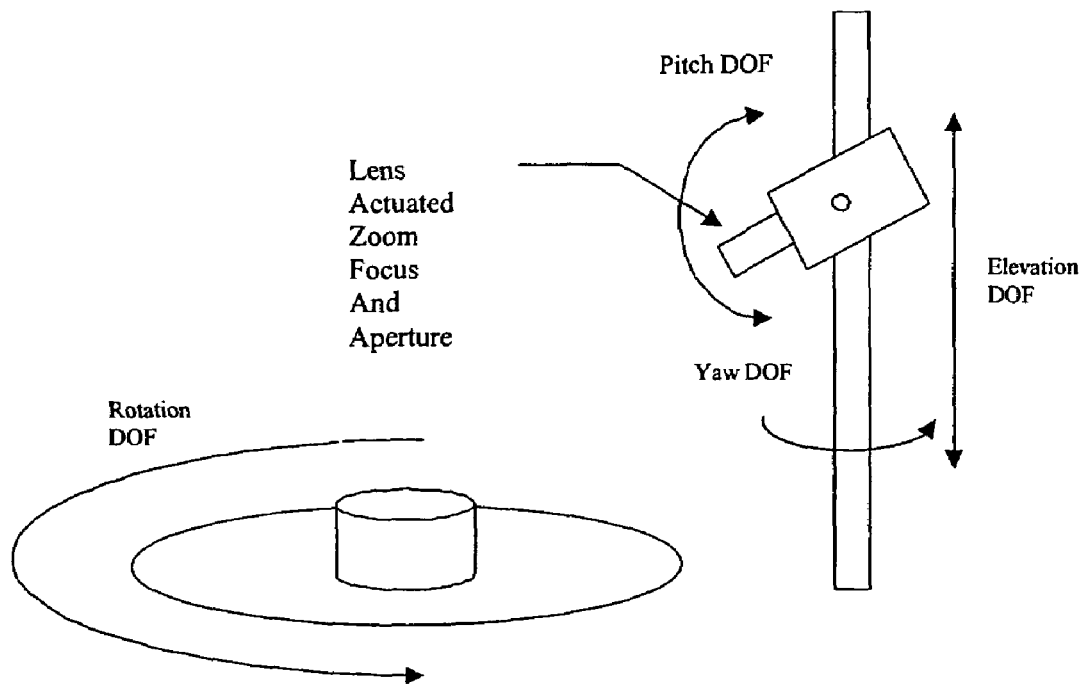
FIG. 8: Illustrates the Cylindrical Turntable Scanner Kinematics realization for the image acquisition system.

A number of different kinematic configurations for the scanner are possible in order to accomplish the acquisition of views from different directions. FIG. 8 illustrates the kinematic articulation for the cylindrical turntable scanner configuration. In particular, the camera elevation degree-of-freedom (DOF) and pitch DOF, as well as the turntable rotation DOF are actuated and computer controlled.

Figure 9:
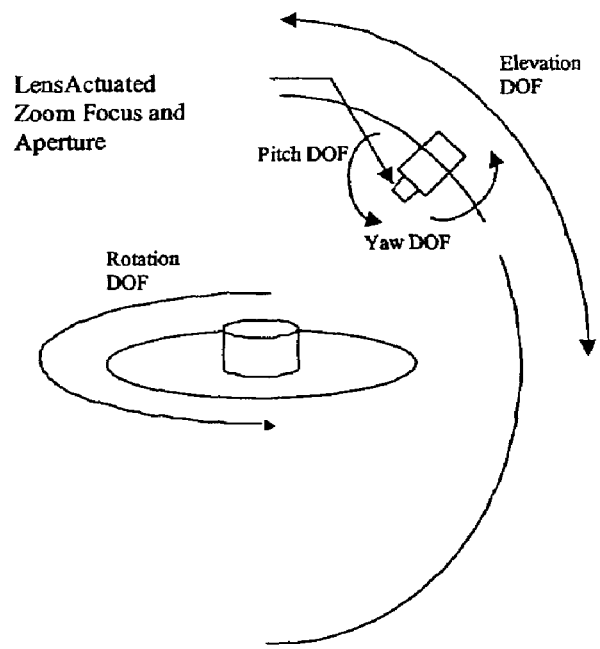
FIG. 9: Illustrates the Spherical Kinematics realization for the image acquisition system.

An alternative view embodiment which constrains the view direction to the origin (center of rotation of the turntable) is illustrated in FIG. 9. In this embodiment, the PITCH DOF and YAW DOF correspond to pan and tilt relative to the current ELEVATION DOF along a given arc support. The Turntable ROTATION DOF is the same as in the cylindrical kinematic configuration.

Figure 10:
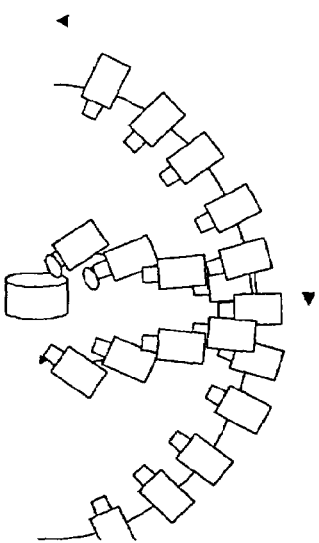
FIG. 10: Illustrates the Non-Articulated View Acquisition Platform realization for the image acquisition system.
Figure 11:
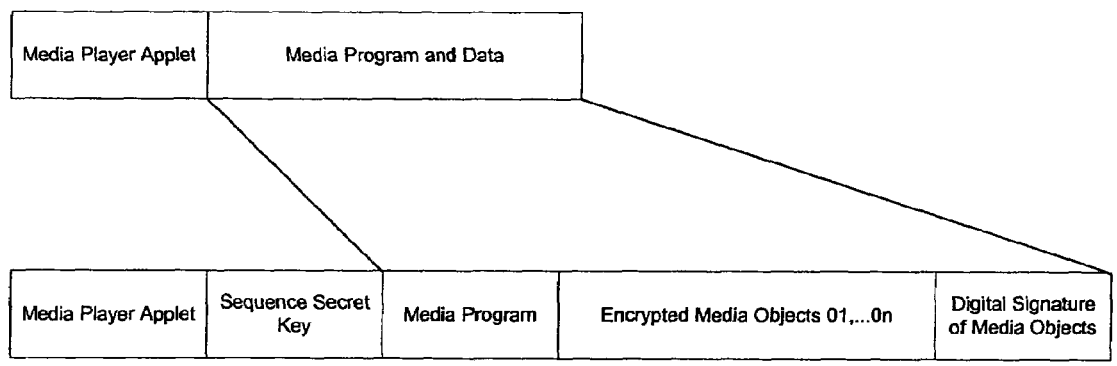
FIG. 11: Illustrates the encapsulation of the media player applet and multi-media object sequence.

If desired, a number of cameras may be laid out in a semi-circular configuration as illustrated in FIG. 10. While more restrictive, this configuration allows for the elimination of any moving parts and simultaneous acquisition in the view sequence acquisition system at the expense of the need for more cameras. Additionally, the set of cameras may be mounted on a serial articulated linkage such as a spiral wound gooseneck, and positioned arbitrarily along a given trajectory to form a particular sequence of views.

Hardware Modules for Self Contained Scanner

Figure 12:
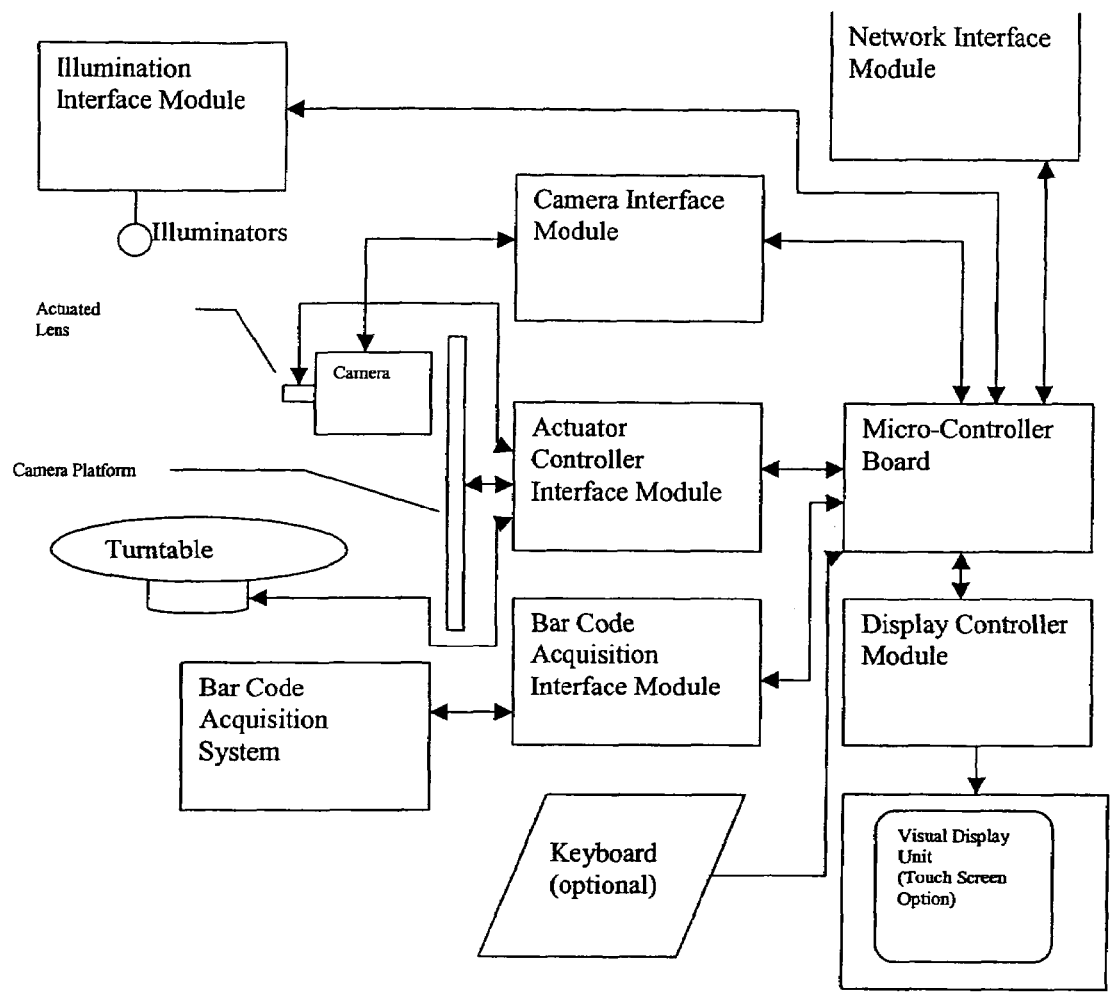
FIG. 12: Illustrates the Self Contained View Acquisition System Kiosk hardware blocks.

In particular such a kiosk would have the following hardware components as illustrated in FIG. 12. A digital camera would be utilized to acquire digitized high resolution color or black and white digital images of the object. The camera would have electronically adjustable gain and integration time which would be achieved by use of a camera interface module. The camera would be fitted with an computer controllable actuated lens would allow for adjustment of zoom, focus and iris. The camera would be positioned on a camera platform which would allow for computer control of the camera height and pitch. A computer controlled turntable (rotational positioner) would allow for computer command of turntable rotational angle. The actuated lens, camera platform and turntable would all be controlled by an actuator controller module. The Illumination Control Module would serve to control the illuminators in the system. The micro-controller board would be responsible for the overall system coordination and control of modules The bar code acquisition system would be used to scan and extract the coded unique object identifier alphanumeric strings which the displayer would bring to the kiosk to identify the object(s) that they are scanning. The bar code acquisition system would be controlled and communicated to via the bar code acquisition interface module. The display controller module would generate any video needed for the graphical user interface and view sequence preview which is displayed on the visual display unit (an LCD or CRT in the preferred embodiment). The network interface module carries out the communication to the network connection which access the application server computer host.

Figure 13:
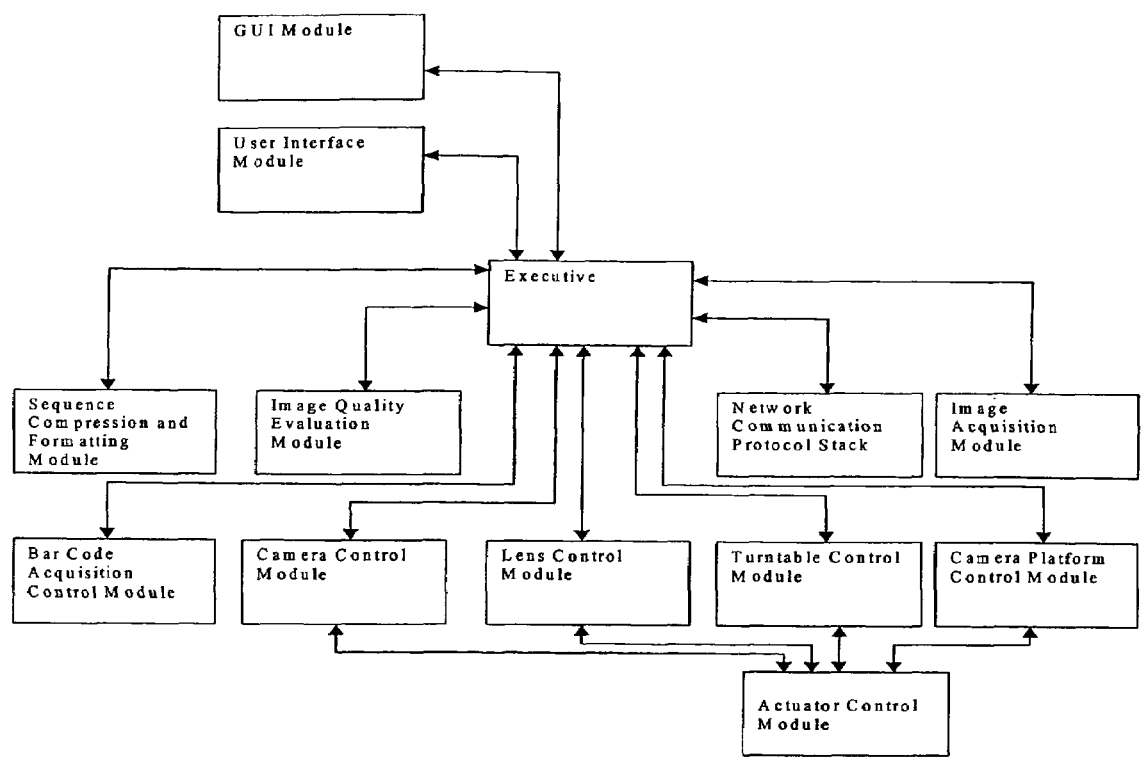
FIG. 13: Illustrates the Self Contained View Acquisition System Kiosk software modules.

The following software modules would be executed by the PC micro-controller board as illustrated by FIG. 13. The executive is responsible for the overall system sequencing, coordination and control of modules. The GUI module is responsible for rendering graphical screen elements and managing user inputs and utilizes the hardware capabilities of the display controller module, the visual display unit and optionally the keyboard or touch screen. The network communications protocol stack manages communications between the kiosk and the Host Application Server as illustrated in FIG. 2. The image acquisition module uses the capabilities of the camera interface module to acquire digital images of the object. The image quality evaluation module processes the acquired images and image sequences and computes figure ground separation of the object being view sequenced, determines the extents of the object in image space, and selects zoom, focus, iris, gain and exposure values for the camera lens and camera to achieve a high quality view sequence. The selected actuator parameter are used by the executive to actuate the system actuators via the lens Control Module, turntable control module, camera control platform, and camera platform control module while synchronizing image acquisitions at the appropriate points. The Lens Control Module, Turntable control module, camera control platform, and camera platform control module in turn use the services of the actuator control module to achieve the actuator control and motion. The resulting complete sequence is the processed by the sequence compression and formatting module. Once the sequence is complete and accepted by the user, the executive uses the network communications protocol stack to establish a session with the application server and then transmits the view sequence along with the unique object identifier which is acquired via the bar-code acquisition control module.

Processing Application

Overview of the Multi-media Authoring Process

Figure 4:
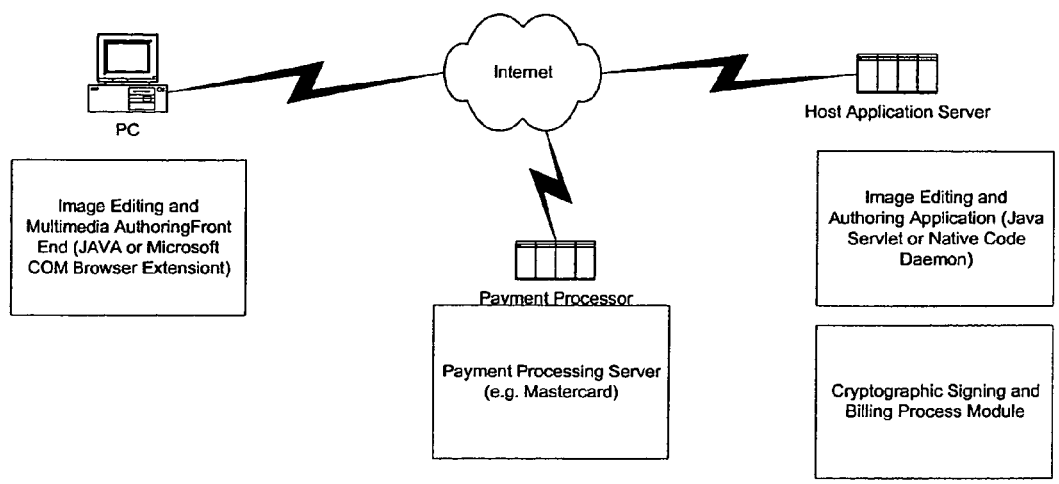
FIG. 4: Illustrates the Network Based Distributed Media Object (Image) Editing and Multimedia Authoring Implementation with a "thin client".
Figure 5:
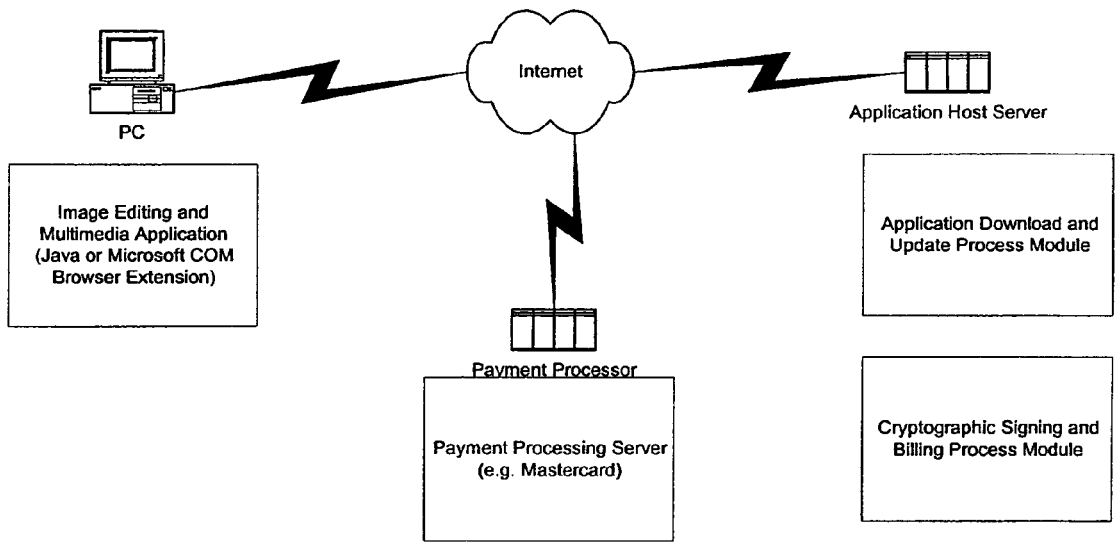
FIG. 5: Illustrates the Network Based Distributed Media Object (Image) Editing and Multimedia Authoring Implementation with a "thick client".

As indicated in FIG. 2, the system consists of a distributed set of processing elements (in the preferred embodiment these are microprocessor based computing systems) connected via a communications network and protocol. The user desiring to edit images or creating multimedia programs uses a client processing element with a display in order to modify images and generate multimedia programs. Taking the elements of FIG. 2 and redrawing them yields an embodiment of such a distributed system is illustrated in FIG. 4, The client computing element may either be a system of low computing capability which merely functions as a display manager as indicated in FIG. 4, or fully capable high computing power workstation as indicated in FIG. 5.

The term author refers to the person involved in the creative editing, enhancement of the images and/or the authoring of the multimedia program which uses those images to yield an interactive multimedia presentation to the end-user of the multimedia program.

Figure 14:
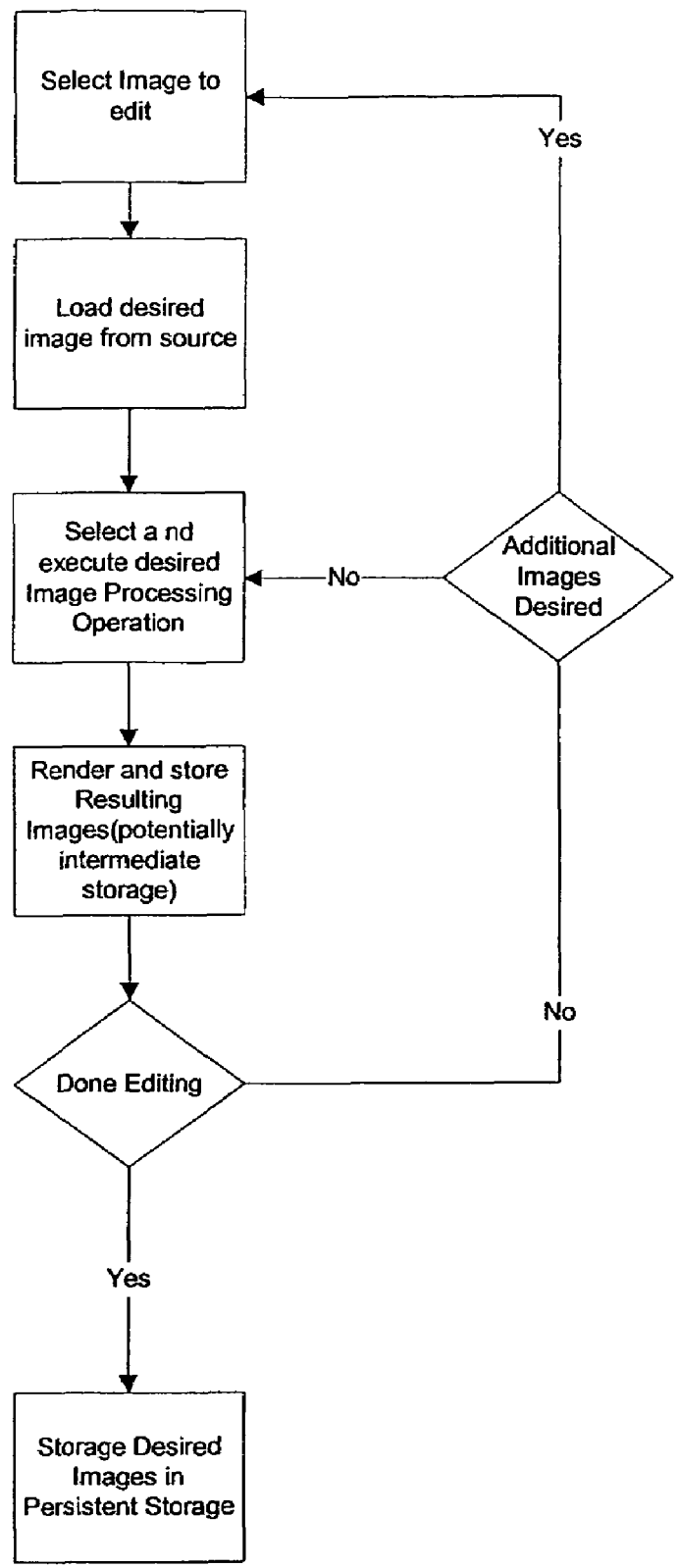
FIG. 14: Illustrates the image editing process for generation of interactive multimedia sequences.
Figure 15:
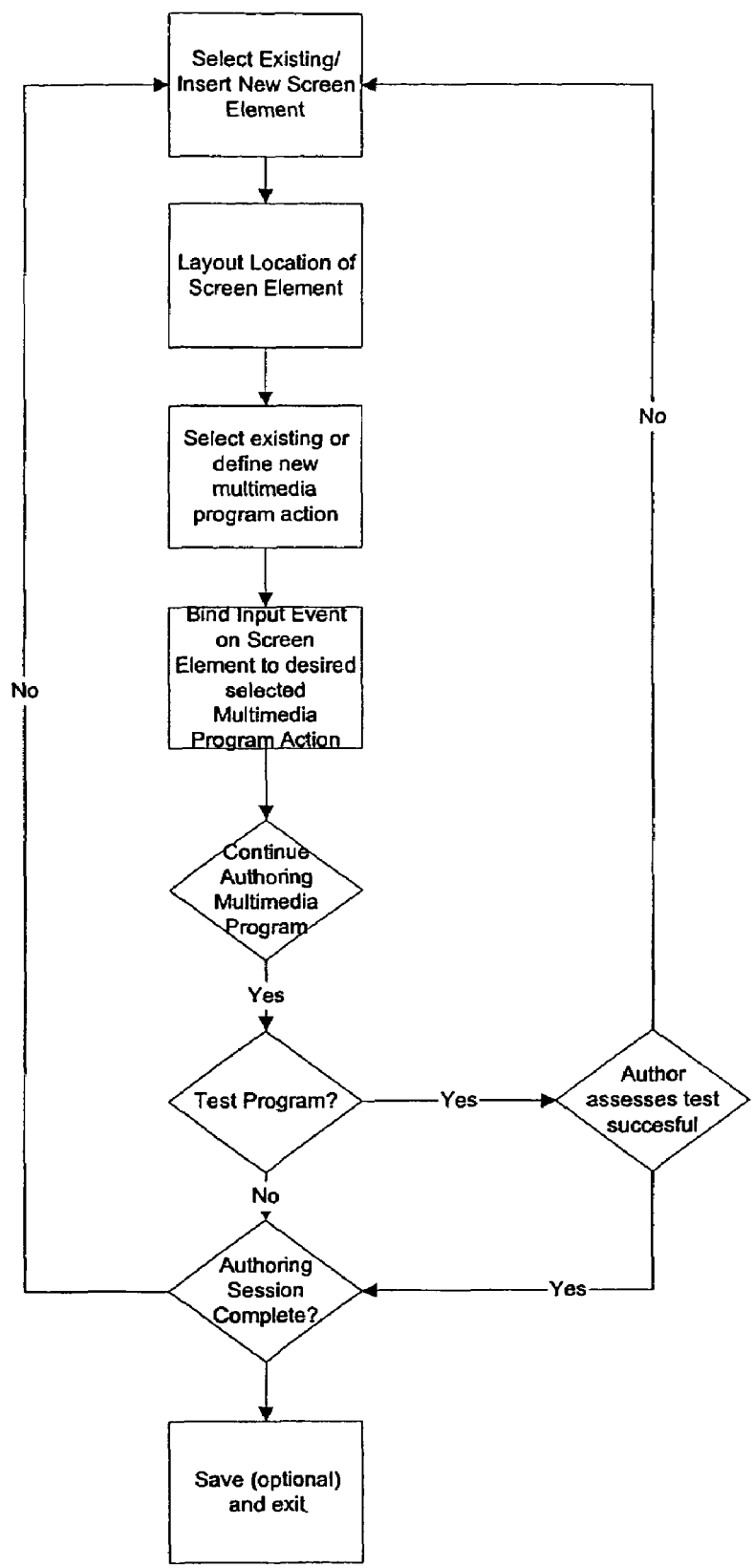
FIG. 15: Illustrates The Multimedia Authoring Cycle for generation of interactive multimedia sequences.

In general to make an interactive multimedia object program, two major functions are needed: digital image processing and enhancement, and creation of the multimedia program which operates on the media objects, such as the digital images, and handles interpretation of user input to create the overall multi-media presentation to the user. The first function ensure that the properties of the images used in the multi-media program meet the requirements of the author. This is commonly known as digital image enhancement and editing and the methods for our system in this regard are described later herein. For example the author may modify the resolution, sharpen the image, change the color palette etc., using a number of well known image processing operations that are common in the prior art. Examples of these operations include contrast enhancement, brightness modification, linear filtering (blurring/sharpening) and thresholding. The select, edit and review cycle for the image processing is depicted in FIG. 14. The second function, the multi-media programming function, consists of writing the multimedia program (or applet), which uses these images along with other input elements media elements such as sounds (the Media objects). The resulting program responds to the end-users inputs by generating output multimedia events. Examples of multimedia events include generation, selection and rendering new images, video sequences, playing digitized sounds etc. in response to these events. The multimedia authoring cycle is illustrated in FIG. 15.

Figure 16:
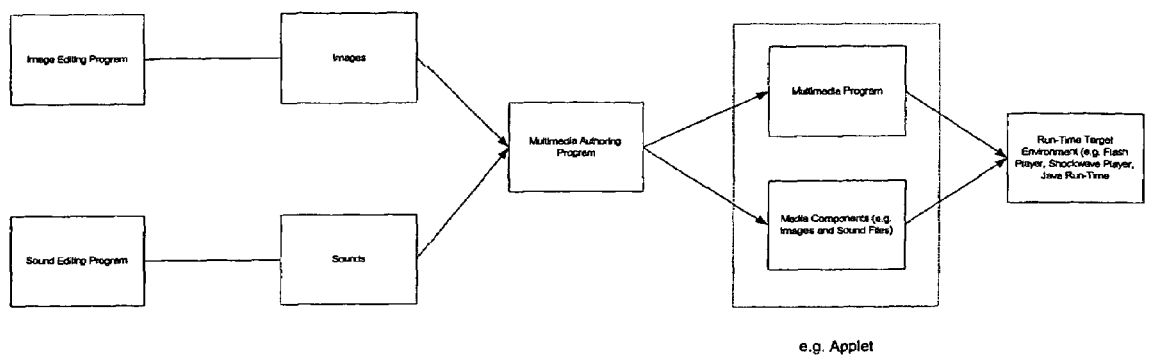
FIG. 16: Illustrates the Editing and Authoring Tools, Objects and Work Flow for generation of interactive multimedia sequences.

A generic overall work flow for the creation of multimedia content is depicted in FIG. 16. Within this overall work flow, a number of implementation and embodiments are possible. For example, the images may be uploaded to a remote server and processed at the server, with the results of the processing being sent back to the client so that the author may see them as in FIG. 4. Alternatively the editing and authoring programs which carry the application and processing of local images and authoring of multimedia programs may be downloaded from a server and used to edit images and other media objects local to the client computer and to form multimedia programs as illustrated in FIG. 5. Furthermore, this application may execute as part of the web browsing program by anyone of a number of well known techniques for extending the functionality of browsers, such as plug-ins and Microsoft ActiveX™ extensions. This allows the users to access the application within their web-browser and within a specific web page, rather than within a separate desk top application.

Specifically, the editing and authoring program may be encapsulated as an extension to a web browsing application by being packaged in the form of a Microsoft COM or ActiveX component, which may be downloaded on demand when a particular page of HTML hosted by the application server is accessed. Furthermore, this application may be signed by the Application's creator using a trusted digital certificate. The application is small in size and can download and install quickly.

Applet Media Player

In this context, the applet is used to manage the rendering and playback of multimedia objects such as images and sounds. These multimedia objects can either be stored on a web server, or encapsulated monolithically with the applet in an archive, such as a Java Archive (JAR) file. Alternatively, these multimedia programs may be encoded in a particular standardized or multimedia script format such as Macromedia Flash Format.

Figure 17:
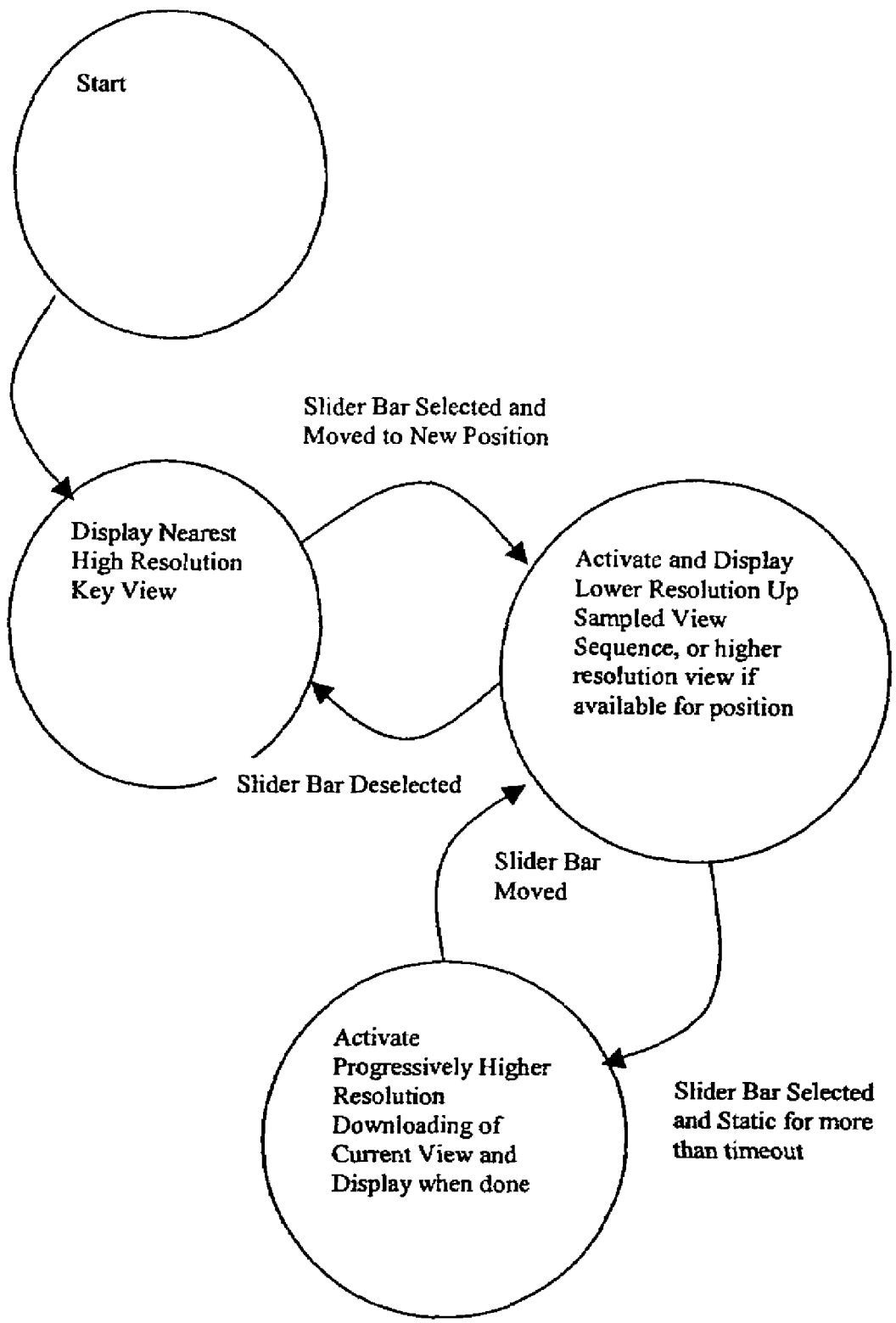
FIG. 17: Illustrates State Diagram for View Applet
Figure 19:
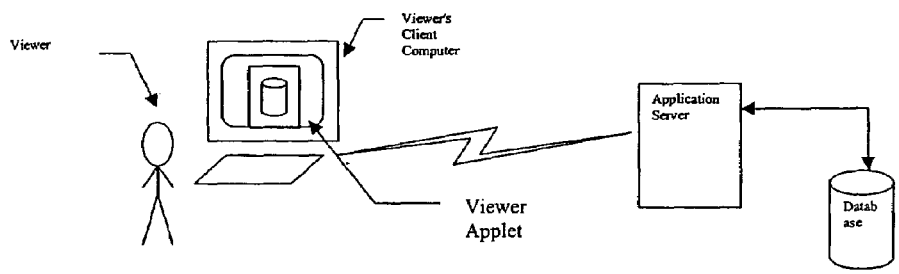
FIG. 19: Illustrates the Direct Viewing of the media sequence from View Host.

As illustrated in FIG. 19, once the view sequence file has been created and stored in the database it may be retrieved via a command to the Storage and Caching server and sent to the viewer's client computer where the a viewer application or applet interprets, unpacks and renders the omni directional views in an interactive fashion. If a user wishes to view a particular interactive omni-directional view sequence, s/he may enter retrieve the sequence of interested from the database to their client computer using the above mentioned unique identifier. Once the view sequence has been retrieved and is available at the client, the viewer may view the sequence using an interactive viewer application program (applet), which allows for the interactive selection of views of the object of interest. The applet consists of an interactive set of on-screen controls which when modified by the viewer, can allow for different views of the object to be selected. In particular by rapidly and smoothly scrolling through a continuous set of views the appearance of smooth object rotation may be achieved and a three-dimensional effect achieved, The state diagram for the viewing applet is depicted in FIG. 17.

In particular, the Application Server may host the image, but the image may be referenced and be indirectly included in the merchants web site via a URL reference in the merchant's web-site. A similar mechanism may be used for a particular posting in a classified ad, or in an on-line auction placement.

An example of the output of a Java Language based viewer applet is illustrated in FIG. 1. The user can interactively slide the slider bar graphical user element to the left or right to cause the viewed object to rotate to the left or right by selection of appropriate views in the view sequence.

Authorization of Content for Distribution and Playback

As mentioned in the introduction, it is desirable to enable the "pay-per-use" distribution of the software application, which permits the creation of the interactive multi-media sequences. In order to ensure the proper licensing of the resulting interactive program, it is desirable that the multimedia program or applet be bound to the set of media objects through the use of a digital signature. The digital signature can be used to check for the integrity of the multimedia object sequence and to enforce the binding of a unique applet or set of applets to a set of multimedia objects and to enforce copyrights etc. This is described in the following section.

In order to enforce the proper consideration (payment) in exchange for licensed use of multimedia programs cryptographic techniques are used to ensure that the multimedia sequences and objects generated have been properly generated in an authorized fashion. In particular, authorization for the interactive viewing of a sequence can be accomplished by checking that a uniquely generated multimedia program is bound cryptographically to a particular set of media objects which it uses as part of its multimedia interactive program.

Secondly, the particular set of media objects can be authenticated (independent of the player) as having been bound together and processed in an authorized fashion which guarantees that payment has been made. If the authorization for the collection of media objects fails, then the player will not play the multimedia presentation. This ensures that user of the multimedia program will only use the media program when properly licensed by the entity which controls the multimedia authoring and imaging editing capabilities.

Binding an Ordered Set of Multimedia Objects to an Applet Using Symmetric Cryptographic Algorithms The Notation used in the exposition is as follows:

Let the message $M=\{O_1, \ldots, O_N\}$, be the ordered concatenation of the set of multimedia objects as encapsulated.

$E_k(M)$ is defined as the encryption of Message M using key k with a symmetric key algorithm e.g. DES 56 bit key.

$D_k(M)$ is defined as the decryption of Message M using key k with a symmetric key algorithm e.g. DES 56 bit key.

H(M) is defined as the secure hash of message M using for example MD-5 Algorithm, although any one of a number of proven secure hash algorithm will suffice.

$S=S_k(M)$ is defined as the digital signature of the secure hash of Message M or shorthand for $E_k(H(M))$, such as using the NIST DES Algorithm in Cipher Block Chaining mode.

$V_k$S) is defined as the validator of the signature S of M or shorthand for $V_k(M)=D_k(E_k(H(M)))=?$ H(M). where H(M) can be independently computed by the validation computer since it is a well known hash function.

Signature w/Non Encrypted Content

In order to bind the applet viewer to a particular multimedia sequence, a symmetric encryption key is embedded in the viewing applet. This key, k is used as the basis of binding the multimedia object sequence to an applet which can view it. The embedding of the key can be accomplished in a variety of different ways, we describe two approaches which can be used in the preferred embodiment. In the first approach, the media player applet byte code and the key file encoding the encryption key k are inserted into an archive such as a Java archive (JAR) file as is illustrated in FIG. 1. An alternative approach is to insert the key value into the Java source code corresponding to the media player applet code and then compile the source code into the Java byte code which has the key embedded.

The encapsulation set consists of applet A(k) with key k embedded within it and M, the ordered sequence of multimedia objects, and S, the signature of the sequence M. This is described notationally as $\{A(k),M,S_k(M)\}$. It is also possible to split apart the archive into the applet and media sequence: $\{A(k)\}\{M,S_k(M)\}$ where $\{A(k)\}$ is on one computing system and $\{M,Sk(M)\}$ is on another computing system. It is preferable to superencrypt the key k with another embedded key, k2, to make it more challenging to extract the key k. The super-encryption key is embedded in the applet as well.

The processing sequence is as follows:

The signing k is generated within the client-side application

The client computes $S_k(M)$

The client sends K and $S_k(M)$ to the server.

The server creates A(k)

The client sends M back to the Application Hosting Server.

The application and hosting server creates the encapsulation $\{A(k),M,S_k(M)\}$ and stores it in the storage and cacheing server.

Signature w/Encrypted Media Set Encapsulation

If it is desired to sign and encrypt the contents of the message M in the encapsulation, the following items can be generated $\{A(k,S),E_k(M),S_k(M)\}$, where $E_k(M)$ represents the encrypted media object M.

The processing sequence to generate these items is as follows:

The signing k is generated within the client-side application

The client computes $S_k(M)$

The client encrypts M, yielding $E_k(M)$.

The client sends K and $S_k(M)$ to the server.

The server creates A(k)

The client sends $E_k(M)$ back to the Application Hosting Server.

The application and hosting server creates the encapsulation $\{A(k),E_k(M),S_k(M)\}$ and stores it in the storage and cacheing server.

Playback

Checking Authorization for Playback (Unencrypted Media)

Figure 18:
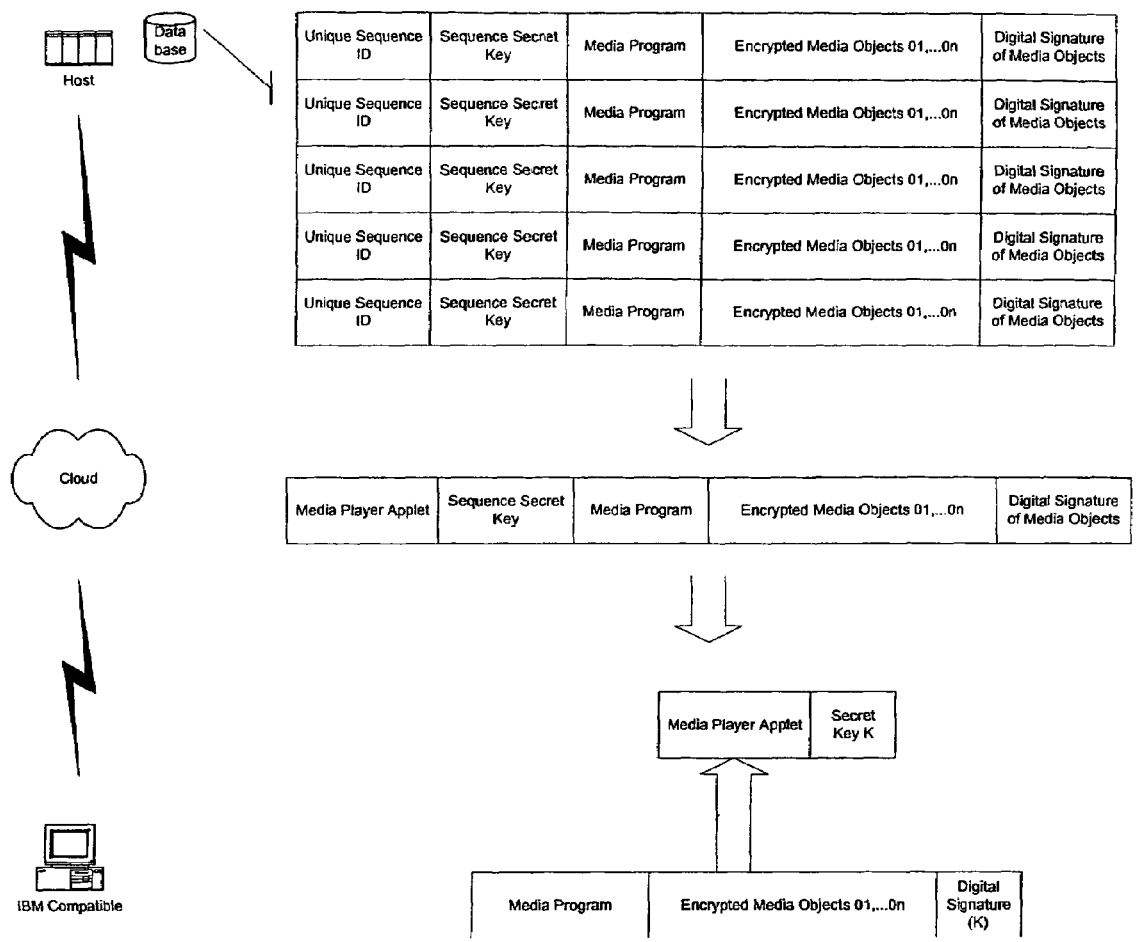
FIG. 18: Illustrates the storage database, transmission and playback of the interactive multi-media sequence.

When the media program is requested, the storage and cacheing server retrieves the matching Applet as indicated in FIG. 18, which results in the data bundle consisting of $\{A(k), M, S_k(M)\}$ arriving at the end-user computer.

Upon receipt of the bundle is split into the Applet with embedded key A(k), the media sequence M, and the digital signature $S_k(M)$.

The applet begins and execution and carries out the following steps:

1. Computes the secure hash H over M, H(M)
2. Computes the Validator H' of the appended media sequence M, where $H'=D_k(S_k(M))=D_k(E_k(H(M)))$.
3. If $H'=H(M)=S_k(M)$, then the computed hash and the decrypted secure hash match. Then message signature is judged as valid and the sequence is displayed, else the applet will not execute the interactive display of the media objects.

Playback (Encrypted Media)

When the media program is requested, the storage and caching server retrieves the matching Applet as indicated in FIG. 18, which results in the data bundle consisting of $\{A(k), E_k(M),S_k(M)\}$ arriving at the end-user computer.

Upon receipt of the bundle is split into the Applet with embedded key A(k), the media sequence M, and the digital signature $S_k(M)$.

The applet begins and execution and carries out the following steps:

Upon receipt of the encapsulation for encrypted media during execution the following sequence occurs:

1. Applet A uses its embedded key k for decrypt the sequence $E_k(M)$, yielding the original plaintext multimedia sequence $M=D_k(E_k(M))$.
2. Applet A computes the secure hash H over M, H(M)
3. Applet A computes the Validator of the Appended Media Signature $H'=D_k(S_k(M))$.
4. If $H'=? H(M)=S_k(M)$ (the computed hash and the decrypted secure hash match) then message signature is judged as valid and the sequence is displayed, otherwise the applet will not execute the interactive display of the media objects.

Single Applet or one to few (per customer key) Sequence Validation via embedded symmetry.

The key k embedded in the applet can be a universal key, where all generated applets contain it. However, if this key is compromised, then new sequences can be generated that will work with applets. Optionally, a "customer key" can be allocated for each entity doing business with the applet generation service. In this case, only that customer's applets will be "cracked", but the key will not be able to generate sequences that work with other customers applets. However, once an applet is "cracked" it can be published along with the key and signing algorithm and allow other to create view sequences out of licensing.

Next, another approach is described below using public key cryptography which is similar in spirit to this approach, but avoids embedding a symmetric key in the applet which could potentially be compromised, thus compromising licensing of all sequences with the common key. Binding an ordered set of multimedia objects to an applet using Public Key Cryptographic Algorithms An alternative approach is to use a public key approach where there is a "company" public key which is well known and published, signed by a certificate authority and also embedded in the applet $A(k_{pub})$ which is universally distributed (at least in a large number of applets) and a corresponding private key $K_{priv}$ which is kept secure and confidential.

Public Key Signature w/Non Encrypted Content

In the sequence creation process, the following steps occur:

1. The client creates a secure hash H(M) of M the media sequence and H(M) is sent to the application hosting server.
2. The client sends M back to the Application Hosting Server.
3. The application hosting server then uses the private key $k_{priv}$ to encrypt H(M) yielding $E_{kpriv}(H(M))$.
4. The server creates $A(k_{public})$, an applet with the public key embedded within it.
5. The application and hosting server creates the encapsulation $\{A(k_{pubic}),M, E_{kpriv}(M)\}$ and stores it in the storage and caching server.

Public Key Signature w/Encrypted Content

In the sequence creation process, the following steps occur:

1. The client creates a secure hash H(M) which is sent to the server.
2. The client creates a symmetric key K which is to be used to encrypt the media sequence.
3. The client encrypts M, yielding $E_k(M)$.
4. The client sends $E_k(M)$.back to the Application Hosting Server.
5. The server then uses the private key $k_{priv}$ to encrypt H(M) yielding $E_{kpriv}(H(M))$.
6. The server creates $A(k_{public}, k)$, an applet with the public key embedded within it, as well as the media decryption key.
7. The application and hosting server creates the encapsulation $\{A(k_{pubic},k), E_k(M), E_{kpriv}(M)\}$ and stores it in the storage and caching server.

Checking Authorization for Playback (Encrypted Media with Public Key)

When the media program is requested, the storage and caching server retrieves the matching Applet as indicated in FIG. 18, which results in the data bundle consisting of $\{A(k_{pubic}), M, E_{kpriv}(M)\}$ arriving at the end-user computer.

1. Computes H(M)
2. Computes $H'=D_{kpub}(E_{kpriv}(H(M)))$.
3. If $H'=H(M)$ then the computed hash and the decrypted secure hash match. Then message signature is judged as valid and the sequence is displayed, else the applet will not execute the interactive display of the media objects.

Checking Authorization for Playback (Encrypted Media with Public Key)

When the media program is requested, the storage and caching server retrieves the matching Applet as indicated in FIG. 18, which results in the data bundle consisting of $\{A(k_{public},k),E_k(M), E_{kpriv}(M)\}$ arriving at the end-user computer. K the encryption key for the media sequence may optionally be superencrypted by a static key embedded in the applet byte code to make the defeating of the algorithm more difficult.

1. Computes H(M)
2. Decrypts $E_k(M)$, yielding M, using key k.
3. Computes $H'=D_{kpub}(E_{kpriv}(H(M)))$.
4. If H'=H(M) then the computed hash and the decrypted secure hash match. Then message signature is judged as valid and the sequence is displayed, else the applet will not execute the interactive display of the media objects.

Billing

The above authorization and authentication techniques provide a convenient means for billing and payment in exchange for creation of multimedia sequences.

The user can authenticate themselves to the applet generation server by providing an authenticator along with S and k generated from the authoring/editing program in the section above. If the authenticator for the user is validated by the server (e.g. the password and userid are a valid combination) then the applet server charges the users account appropriately for the requested service and goes ahead and creates the applet. Payment may be by a credit card transaction, or by debiting credits on record for that particular user using the payment processor illustrated in FIG. 5.

In an alternative embodiment, signed credits may be sent down to the client station in a lumped set. The authoring application may be given the authority to generate applets and sign media sequences using the techniques described in the previous sections. The signed credits consist of random numbers (Nonces) that are signed by the public key of the applet generation service. The client side generator validates the credit using the local copy of the applet generators public key. If the validation succeeds, then the applet may be generated and media sequence signed using the credit.

The credit file is encrypted using a symmetric key which is embedded in the generator application which has a unique serial number. Key agreement between the client-side and the server side can be done using Diffie-Hellman key agreement. Whenever the client-side generator needs to generate a new applet it decrypts the file, reads the index for the last used credit and increments and then validates the public key signature of the next credit. If it succeeds, then it uses the next credit nonce as the key k for the generated sequence in the techniques above for authentication and authorization. The index in the file is updated to point to the next record and the file is resigned using a message authentication code and re-encrypted. Alternatively it may use the public key signing approaches described in the previous sections.

Image Processing

Masking Techniques

The identification masking of background from foreground objects of interest is often desirable in photography, such as for example, in catalog photographs. Once the foreground and background are identified, a number of other image special effects are also possible. In addition to making of the background, a digital matteing processing can be done which generates a composite image. The composite image is composed image sources from two or more images. Regions identified as being one type (e.g. background) are substituted with source images information from another image, while regions identified as another type (e.g.) foreground are not modified. This can allow for synthetic backgrounds to be substituted with other desirable images. In the art the identification of foreground and background has been done using a variety of means. For example it has been done manually by hand masking tools within digital editing programs, which can be a tedious and time consuming process to do properly. Other common approaches employ using colored backgrounds which can be identified through computer or video processing and automatically detected (Chroma-key techniques). However Chromakey techniques have the disadvantage of requiring large and cumbersome background backdrop of a particular color, which often must be changed to make sure the background color is of a particular shade that is not contained in the foreground object of interest. We present two techniques, image subtraction and motion segmentation which avoid these inconveniences.

Automatic Background Removal Using Image Subtraction

Background Identification

In general, given two images, one with a foreground object and the other without, the background areas which are taken under similar scene illumination and camera setting, will have very similar color or gray scale values in the situation with and without the foreground object, whereas areas that contain the foreground object in one image, but not in another will have a large absolute difference.

This large absolute difference or vector difference magnitude will indicate the presence of a foreground object of interest. By selecting pixels which are above a relatively small threshold in terms of gray level or color magnitude (brightness), a mask can be formed which selects only foreground object pixels.

In the case where the background scene is complex and cluttered it is important to align the two images. This ensure pixel-to-pixel correspondence between the two images. If this is not done it may cause errors. The alignment can be done in two ways, the first being to mechanically align the two images during the acquisition step by making sure the camera is held fixed, such as on a tripod. The second way is to employ electronic stabilization, either within the camera, to track and align the background between two scenes, or after the acquisition, where identical background features in the two backgrounds can be matched, and the backgrounds aligned using affine or other warping techniques.

In these document $|P_i-P_j|$ refers to either the grey-scale absolute difference or color space vector difference depending on whether the image set is color or monochrome with out loss of generality.

The per-pixel gray-scale difference is defined as $D(x,y)=|I_1(x,y)-I_2(x,y)|$ where D(x,y) is the pixel grey value in the difference image D at location x,y, and $I_1(x,y)$ and $I_2(x,y)$ refer to the pixel grey value at the x,y coordinate in the input images 1 and 2 respectively.

Figure 20:
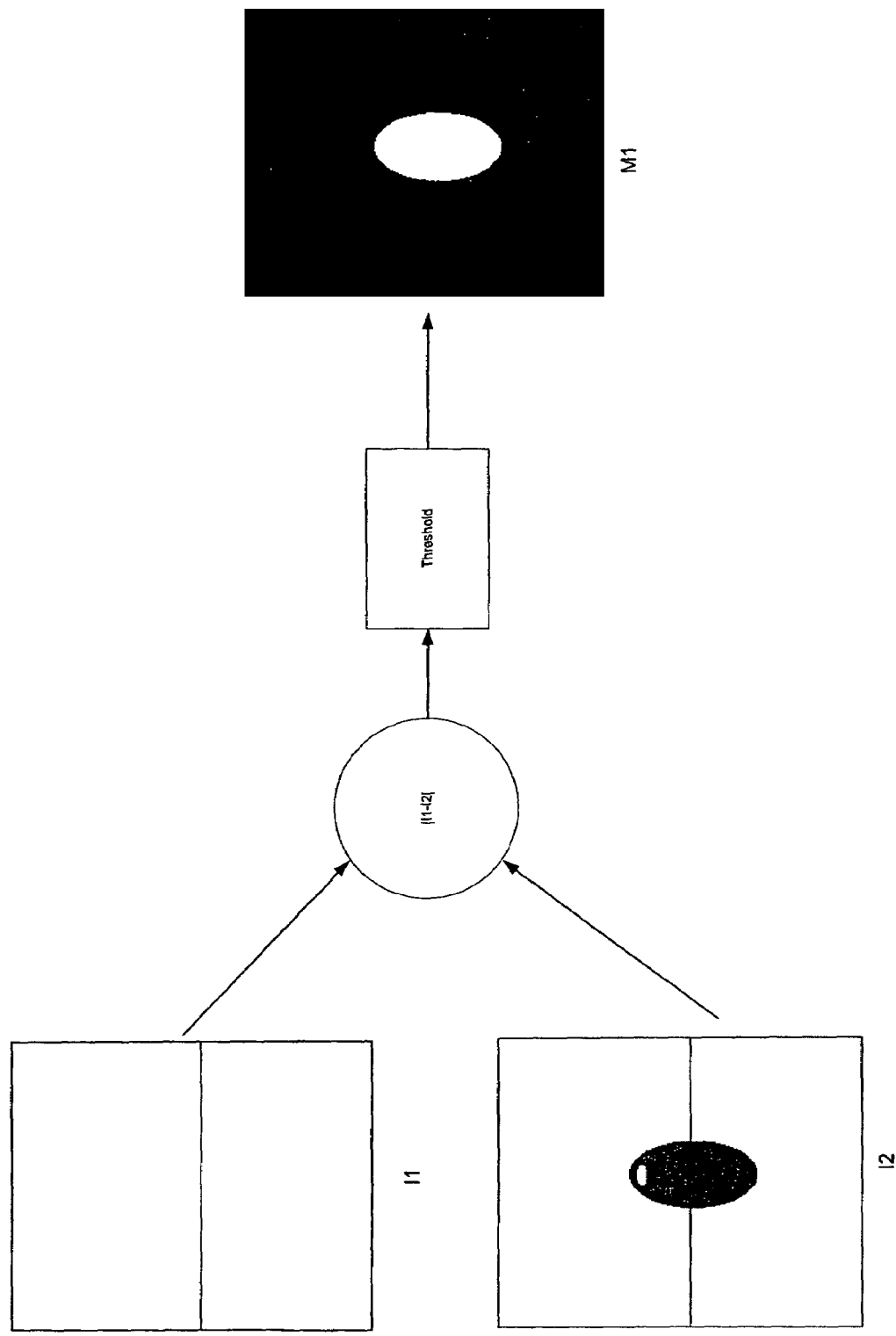
FIG. 20: Illustrates the image differencing process for identification of the image object of interest.

In the case of color images, the magnitude of the difference of the RGB vectors may be used as illustrated in FIG. 20. More specifically, let $I_R(x,y)$, $I_G(x,y)$ and $I_B(x,y)$ be the R,G,B components of a pixel in an image at coordinates x,y, and let $I_{RGB}(x,y)$ be the color vector for the pixel at coordinate x,y. Let $D_{RGB}$ represent the color vector at coordinate x,y in the color difference image. The color vector difference is defined as $D(x,y)=|I_{1RGB}(x,y)-I_{2RGB}(x,y)|$, where $I_{1RGB}(x,y)$ and $I_{2RGB}(x,y)$ represent the pixel-wise RGB vectors for input images 1 and 2. Here the "−" operate represents the vector difference operator, and the "|" represents the vector magnitude operator of a vector.

The background identification process may be automated using a sequence of image processing steps as follows.

1. A picture $P_0$ of the scene without the foreground object of interest is digitized.

2. The foreground object is placed in the scene and another picture $P_1$ is digitized.

3. A third synthetic image $D_1$, which consists of the pixel-wise absolute difference $|P_0-P_1|$ is formed.

4. $D_1$ is then thresholded automatically using an automated histogram derived thresholding technique The resulting image is a binary mask image $M_1$ where all pixels above a certain magnitude are marked as "1" meaning foreground, otherwise they are marked as a "0" for background.

Figure 21:
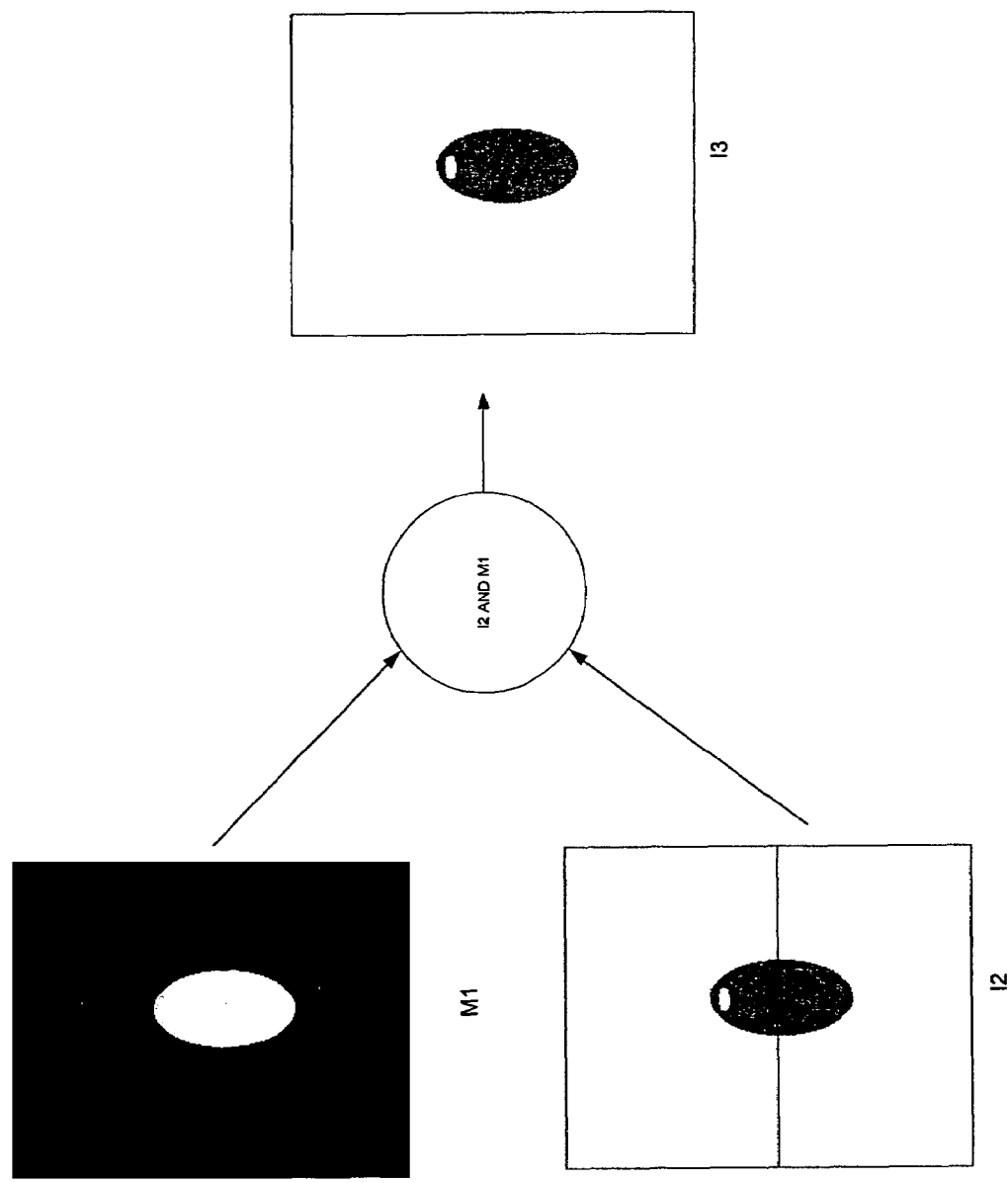
FIG. 21: Illustrates the background masking process for using the image mask.

The mask is applied by scanning each Mask pixel $M_1$(x,y). Whenever the mask pixel takes on the value "0" (background) the corresponding the pixels at coordinate (x,y) in the input image $P_1$(x,y) is set to the default background intensity or color value (See FIG. 21)

Figure 22:
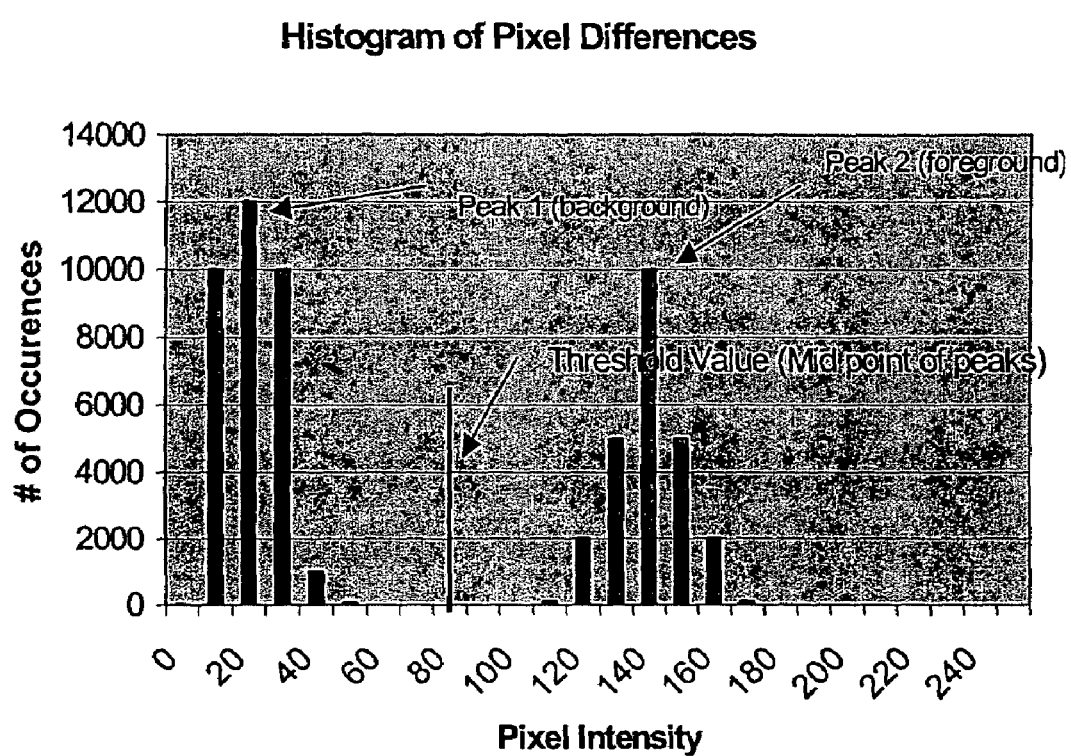
FIG. 22: Illustrates the Foreground/Background Histogram for automatic threshold determination.

In step 4 above, anyone of a number of bimodal automated histogram threshold selection techniques may be used. The bulk background difference from where both images have background will represent the first large uniform spike in histogram from the background having a low magnitude value followed by other peaks at higher values due to regions in the image that come from the difference of the foreground and background objects. For example, a peak finding operator may be applied to the histogram to identify all peaks (intensity values with smaller # of occurrence neighbors) and the threshold set between to the smallest peak and the next largest peak (See FIG. 22).

It is often necessary to carry out a morphological dilation operation to suppress small impulsive holes in the absolute difference mask and to extend the object boundaries for feathering smooth edges.

Matteing Process

This mask can then be logically ANDed with $P_1$ (the image with the foreground image) to form a resulting composited image with the background removed entirely or substituted with other image data if desired. By using an ANDING operation all non-foreground pixels are suppressed, thus suppressing the background. In order to add in a composited background, the logical complement of the selection mask ($M_1'$=logical inverse ($M_1$)) is used to select pixels which are from the background and may be substituted pixel-wise for pixels from the desired new background image which can be a synthetic or natural scene image from another source.

Soft Blending

The binary masking process can be generalized to a soft continuous blending of source images as follows.

Figure 23:
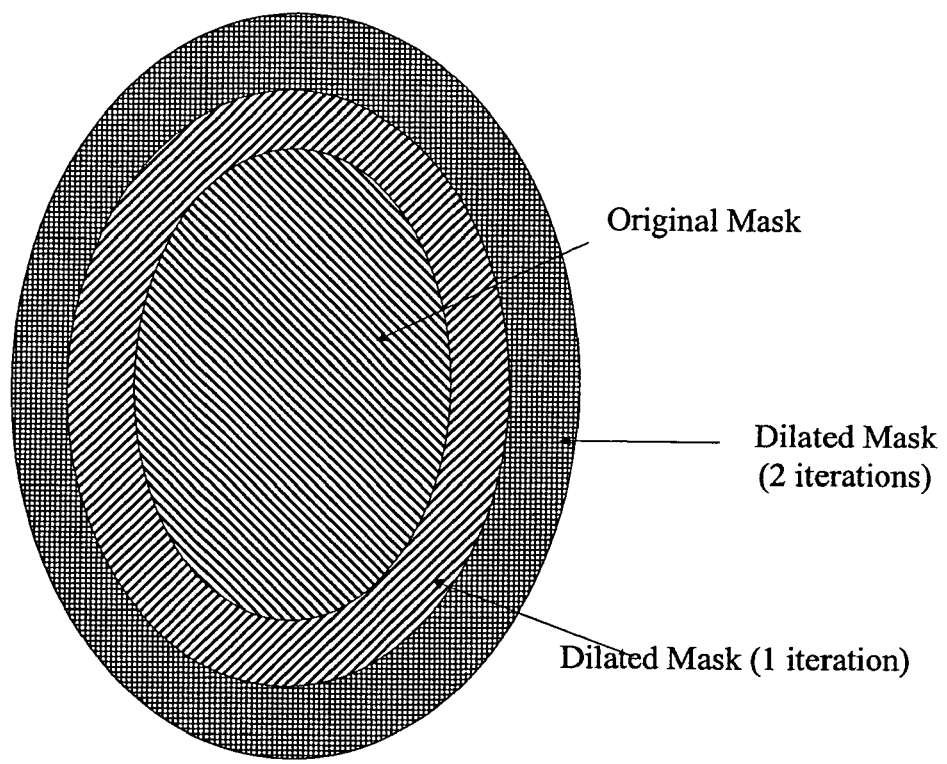
FIG. 23: Illustrates the Dilation Shells of Selection Mask.
Figure 24:
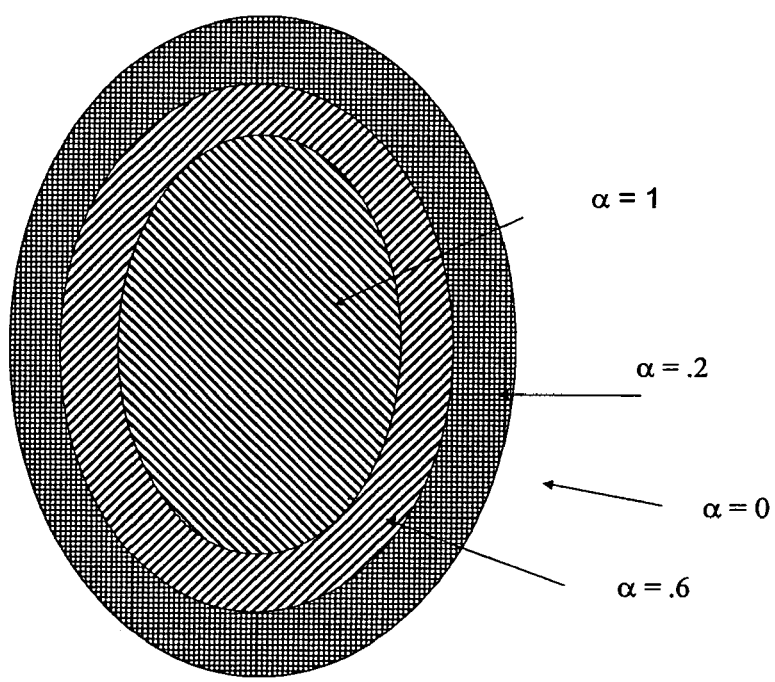
FIG. 24: Illustrates the Alpha Assignments for Dilation Shells.

In the preferred embodiment, image $M_2$ is formed which is the dilated version of the original mask image $M_1$. Then $M_2$ is logically exclusive OR'd (XOR) with $M_1$ to form a shell boundary region mask as indicated in FIG. 23, to form the mask shell $M_2'$ The mask $M_2$ can be dilating yet again to yield $M_3$ and the resulting shell mask $M_3'$ can be formed as $M_3$ xor $M_2$. In general the shell mask for the nth iteration can defined as $M_n'=M_n$ xor $M_{n-1}$. For each shell mask, a blending coefficient $\alpha_n$ is associated in a table.

The blended image $P_b$ results from the pixel-wise linear combination of images $P_i$ and $P_j$. For each pixel in of all possible coordinate values x,y, the coordinate will be an element of one of the Mask shells $M_0, \ldots, M_n$ or the background. In the case the coordinate x,y is an element of $M_n$, then the corresponding blending coefficient an is selected. The blended image pixel is set as $P_b(x,y)=\Box P_i(x,y)+(1-\Box)P_j(x,y)$, the linear combination of pixel values from the two source images.

A convenient way to set $\Box_n$ is $\Box_n=N/N_{max}$ where $N_{max}$ is the maximum number of dilation iterations.

Optical Flow Segmentation Based Background Identification

Another approach for the automatic determination of the object background is to use a optical flow thresholding technique. This approach can be used in the case when the object having some visual pattern or texture, is placed on a textureless rotating platform in front of a fixed camera, and the background of the object is stationary. The background may be flat or textured, as long as it is stationary between acquisitions. In this case, the images space will have a static background with only the object and its support surface (the rotating stage) in motion. If the rotating platform is a flat featureless surface, although it is moving, it will not generate any signal that can be picked up by the camera and will appear motionless.

Optical flow is defined as the spatial displacement of a small image patch or feature over a sequence of frames taken at different times, $$\left(\frac{dx}{dt}, \frac{dy}{dt}\right).$$

Figure 39:
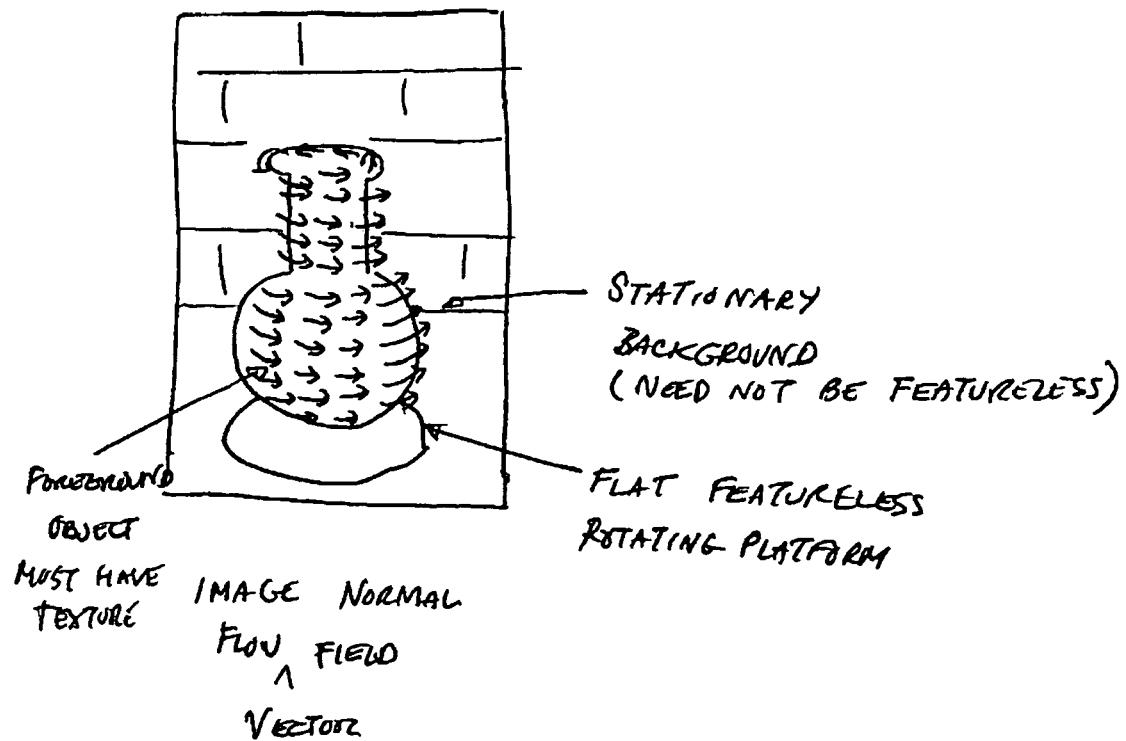
FIG. 39: Illustrates the motion field object of the object of interest and static background.

There are number of techniques in the prior art for calculating this value. Any one of a number of well known optical flow or motion extraction techniques can be used to operate on the sequence and compute the flow on a per-image basis. The flow can be computed using the frame of interest and adjacent frames, including the previous and/or succeeding frame, or extended adjacent sequences. Alternatively, simple image differencing may be used between succeeding frames if more computational simplicity is needed. In this case, instead of a displacement vector $$\left(\frac{dx}{dt}, \frac{dy}{dt}\right),$$

a simple time derivative of image point x,y can be computed $$\frac{d}{dt}I(x,y)$$

and thresholded. The flow magnitude or time derivative is computed at each image point x,y, and magnitude field is created. The flow field for a representative image is illustrated in FIG. 39.

It is possible to compute local optical flow fields, by taking frames with only a small relative object rotation between each frame and computing the pixel-wise or patch wise local motion flow vector of the sequence. This can be done either with a camera, or through the use of a video sequence. Since only the object of interest will be moving in the sequence, pixels belonging to it will have a much higher optic flow magnitude, or time derivative, as they case may be. This constraint can be used to identify all pixels belonging to the object of interest in the sequence.

To summarize, for each image in the time sequence of images the steps in the above approach are:

1. Compute optical flow or time derivative for each pixel of each image in the image sequence. This will yield a flow vector (magnitude and direction for each pixel).

2. Compute the magnitude for each pixel if the optical flow measure is used.

3. Threshold and label each pixel in the flow field with flow vector magnitude greater than threshold Θ. The threshold can be established using any one of a number of automated threshold detection techniques which work with bi-modal value distributions. Alternatively, a fixed threshold may be used.

4. This pixels selected as background can be used in the compositing process where every pixel at x,y marked as background in the matte mask selects pixels in the corresponding inserted background image at location x,y. The combined image will then contain the object in the foreground and the inserted artificial background from the composited background image. The soft blending technique described herein is applicable.

Alignment

In the case that a freehand sequence of shots are taken by walking around a fixed object camera motion may cause rotation of the desired object and non-uniform distance and camera pose may cause the object to move in the composition of the acquired image sequence. In this case it is desirable to allow the person forming the multimedia 3D sequence to scale, rotate and translate the foreground object of interest (known as rectification of the image sequence), so that as the sequence is viewed in the complete multimedia program it presents in a more smooth form.

Visual Displays

The superposition and rectification sequence can be facilitated by a number of visual displays, such as performing edge extraction on the image sequence and superimposing adjoining or neighboring image pairs in the sequence to allow for fast visual inspection of coinciding scale, rotation and translation.

Preview

A sliding preview can be used to step through the image sequence and rapidly detect outlying values of scale, rotation and translation. As the person creating the sequence sees the jumping outlier, the offending frame may be marked for subsequent alignment.

Semi-Automated Alignment Using Affine Transforms

Easier to use Semi-automated approaches to registration can be carried out by allowing the person carrying out the editing to select corresponding planar patches in adjoining images and the using geometric matching techniques to correspond features in the regions and recover the affine transformations between the patches. The affine transform or portions thereof (such as the rotational, scale or translational components) can be used to rectify the images by ignoring the projective (perspective) components.

The Alignment Wizard

The goal of the advanced editing functionality is to allow the end-user to correct for any errors that occurred during the camera picture taking process, especially when a hand held camera was used to take the images.

Using a hand held camera can lead to errors in the centering, orientation and scale of the desired object. This can cause jumpiness and other discontinuities when the final image sequence is viewed interactively. While it is not possible to correct out perfectly for these errors, since that would require the full three dimensional structure of the scene, two dimensional operations on the resulting images can be quite helpful. These problems can reduced to a great extent by the application of image-space transformations including the rotating images, scaling images and translating images so that they are rectified (aligned) to the best extent possible to reduce these effects. There are a number of approaches in principal for specifying which scaling, translation and alignment operations, in which order and with what parameters. They range from approaches which are fully automated, to fully manual, to hybrids of the two. Additionally, any manual operations inevitably involve judgment from the end-user. Therefore an easy to use and intuitive tool set that guides the end-user in the rectification process (an alignment wizard) is highly desirable. Below, we describe a design for an alignment wizard.

The overall functional steps for the wizard are as follows:
1. Rotational Rectification
2. Translational Rectification
3. Scaling Rectification
4. Autocrop The user interfaces, actions and other displays functional requirements are described in more detail below.

Rotational Rectification

Figure 25:
FIG. 25: Illustrates a raw acquired image of the object of interest.
Figure 26:
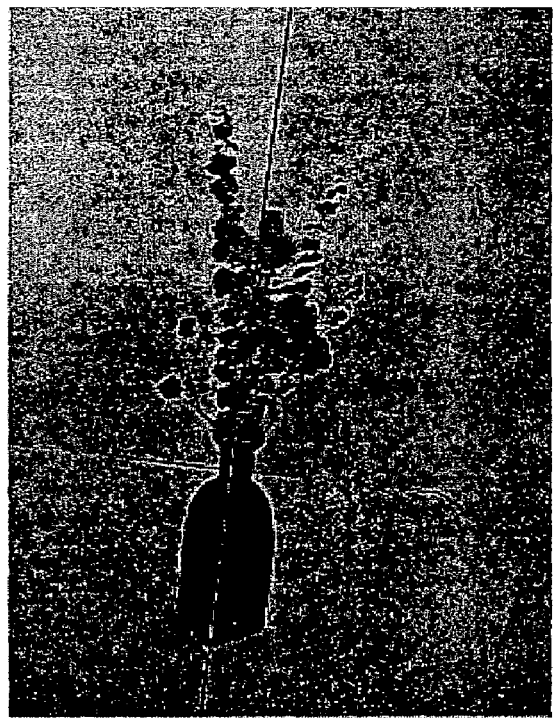
FIG. 26: Illustrates the selection indicator the desired axis of rotation of the object of interest for a first view.
Figure 27:
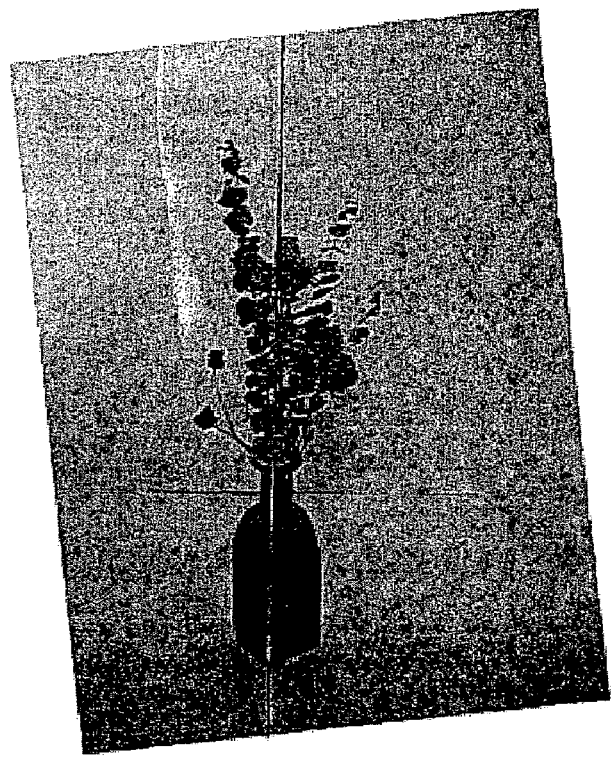
FIG. 27: Illustrates the rotationally rectified desired axis of rotation for a first view.

Given two or more images in the sequence, each taken from a different viewpoint, each image may have been taken with differing roll angles about the optical axis of the camera. This roll can cause an apparent rotation of the object of interest (See FIG. 25) for an example. Since we desire to have the object rotate about its natural axis of symmetry, or some approximation thereof, the first step is to indicate the location of this axis in the image space. This is done by using a line drawing tool to draw a virtual axis of symmetry line in the image of interest superimposed on the image (See FIG. 26). Since this axis of symmetry is generally perpendicular to the floor, the system can now compute the angle of the indicated line and counter rotate the entire image automatically so that the indicated axis of symmetry is parallel to the y-axis of the image frame, as illustrated in FIG. 27. Since a rotation operation requires a natural center of rotation, about which the rotation takes place, this must be selected. This can be done automatically by using the assumption the photographer approximately centered the object when the photo was taken. In this case the mid-point of the indicated axis of symmetry line is a good candidate for the center of rotation.

After the rotation, the image is also translated horizontally in the x-axis direction such that the virtual axis of symmetry is centered laterally in the preview image x-axis coordinate system.

Figure 28:
FIG. 28: Illustrates the selection indicator the desired axis of rotation of the object of interest for a second view.
Figure 29:
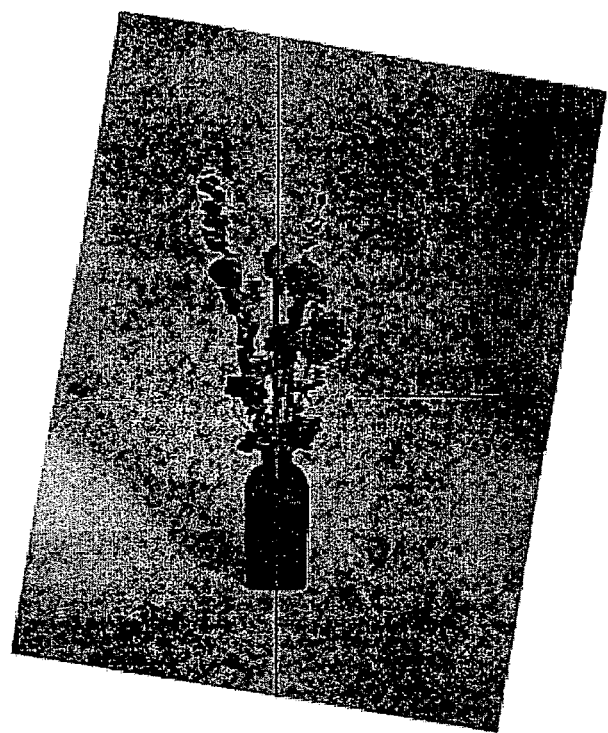
FIG. 29: Illustrates the rotationally rectified desired axis of rotation for a second view.

The above process is carried out by the user for each constituent image in the sequence and this completes the rotational rectification step. For clarity, a second input image (See FIG. 28) and resulting aligned image is illustrated in FIG. 29.

Translational Rectification

Now that the images are approximately aligned from a rotational standpoint, the next step is to adjust for any vertical offsets between the objects locations in the images (The horizontal offset is taken care of by the final lateral translation in the Rotational Rectification Step).

Figure 30:
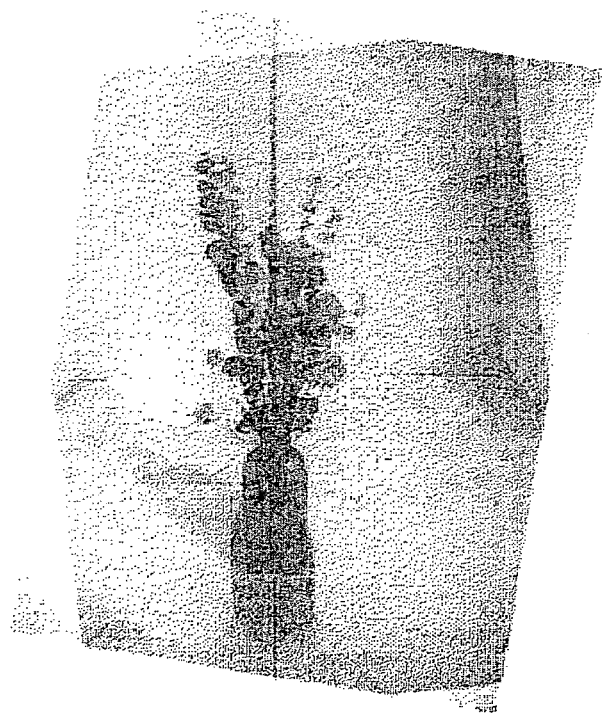
FIG. 30: Illustrates the superimposition of the rotationally rectified first and second views.
Figure 31:
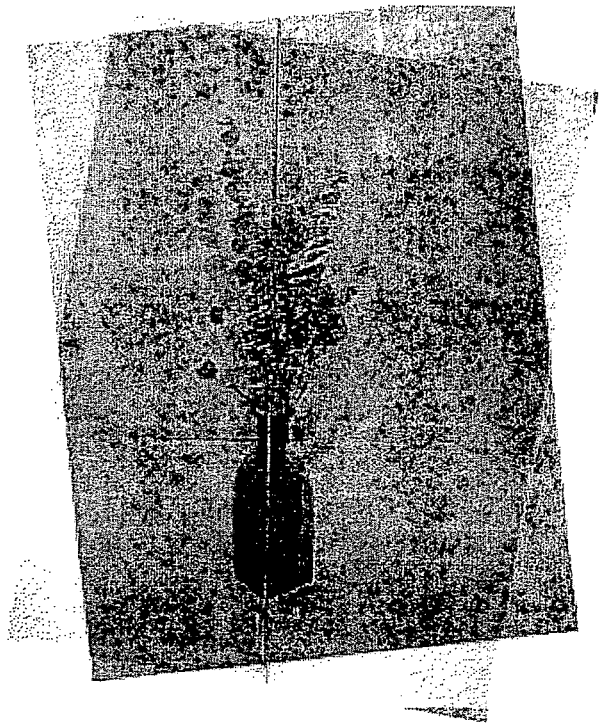
FIG. 31: Illustrates the vertical translation rectification of the first and second views.

This is done using an animated jog effect, where the two images to be rectified are alternatively double buffered and swapped automatically on a ¼ second interval, or value close to the flicker fusion frequency for human perception, which provides visual persistence of each image and a transparency effect where both images are effectively superimposed (See FIG. 30). A user interface mechanism (e.g. a slider oriented in the image y-axis direction) is provided for each of the two respective images to adjust the y-offset of the respective image. When the user is satisfied with the offset, a "done" button is hit to lock the alignment. The result is shown in FIG. 31.

This process is repeated for each consecutive pair of images in the sequence, if needed.

Scaling Rectification

Now that the images are approximately aligned and translated, the final rectification step is to adjust for any variations in object scale that might have occurred due to variations in camera range to the object during the photo shoot.

This is done using an animated jog effect, where the two images to be rectified are alternatively double buffered and swapped automatically on an approximate ¼ second interval (or value close to the flicker fusion frequency for human perception), which provides visual persistence of each image and a transparency effect where both images are effectively superimposed.

Figure 32:
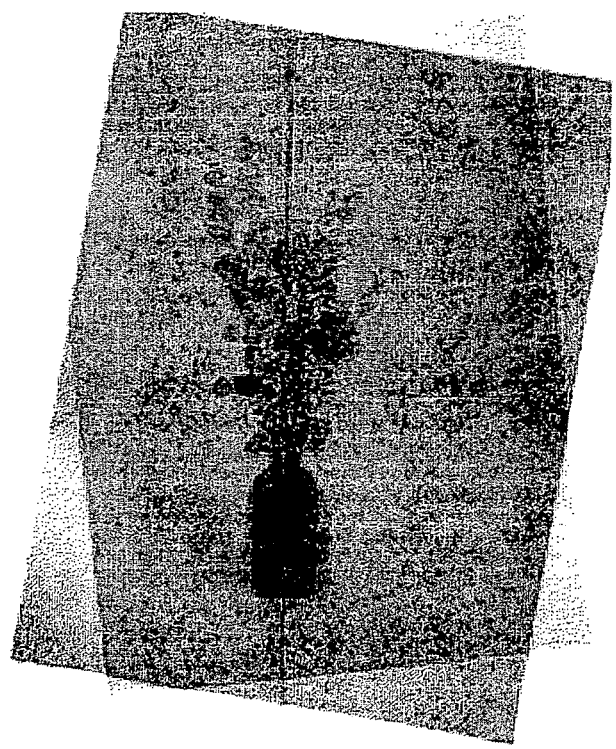
FIG. 32: Illustrates the scaling rectification of the first and second views, using the scaling operator center coordinate indicator.
Figure 33:
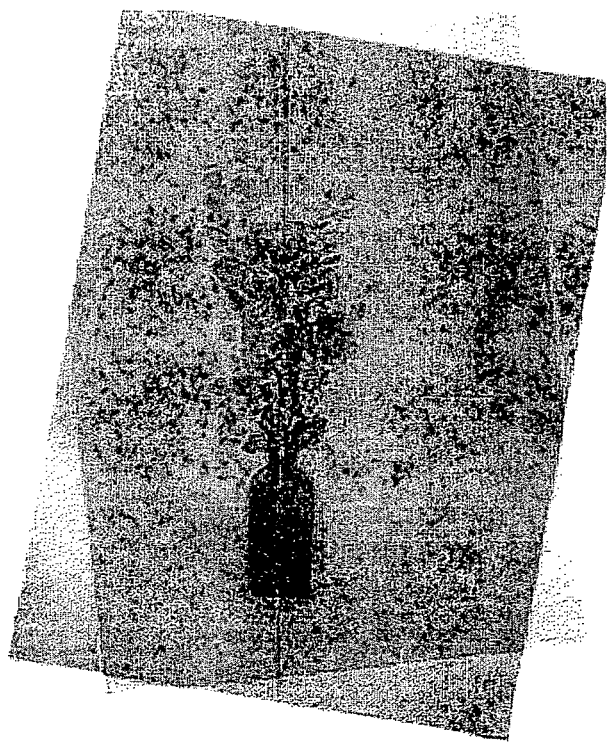
FIG. 33: Illustrates the final results of the rotation, translation, scaling rectification steps.

For scaling, an origin of the scale must be defined. The y-axis center of the scaling is constrained to lie on the axis of symmetry line, which leaves only the selection of the x-axis value for the center of rotation. This location can be indicated by a sliding center point as indicated by a cross-hair in FIG. 32, which can be moved along the virtual axis of symmetry line by the user using direct mouse manipulation. The aspect ratio is fixed for this scaling operation. The result is illustrated in FIG. 33.

Auto Crop

After the above sequence has been carried out on the entire sequence in a pair wise manner on adjacent images, the resulting sequence may have odd borders and gaps in the image due to the applied rotation, scaling and translation operations. It is desirable to crop the images to a minimum inscribed rectangle which eliminates the odd perimeter and image gaps. This can be done automatically in the following fashion.

Figure 34:
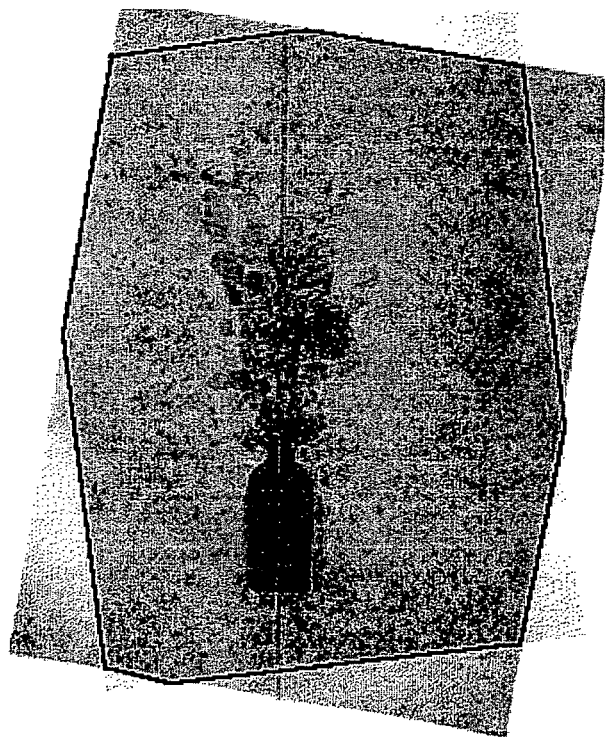
FIG. 34: Illustrates the perimeters of the convex intersection of the areas of views.

First, the intersection of the current image areas is computed automatically. This perimeter of this intersection is a convex polygon, as illustrated in FIG. 34, for two images. While this illustration is for two images, the approach described here applies for more than one image.

Figure 35:
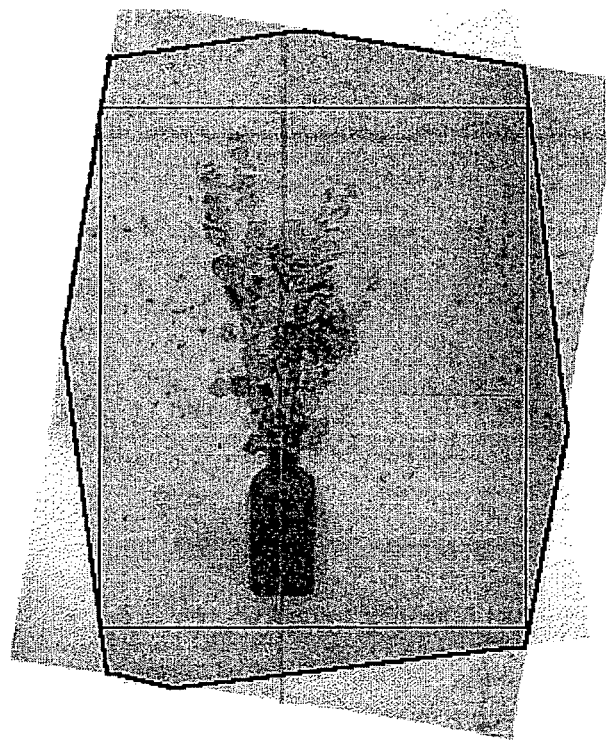
FIG. 35: Illustrates a rectangle inscribed n the intersection perimeter.
Figure 36:
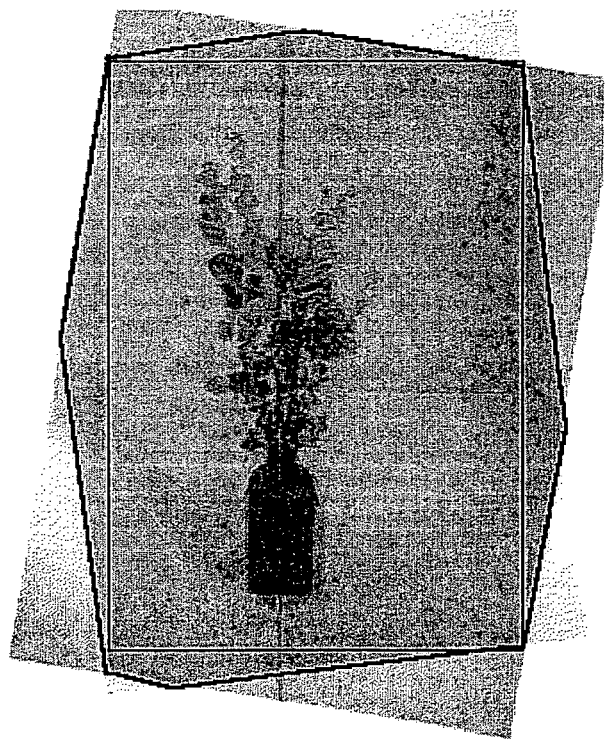
FIG. 36: Illustrates the maximum area inscribed rectangle for the intersection area of multiple views.
Figure 37:
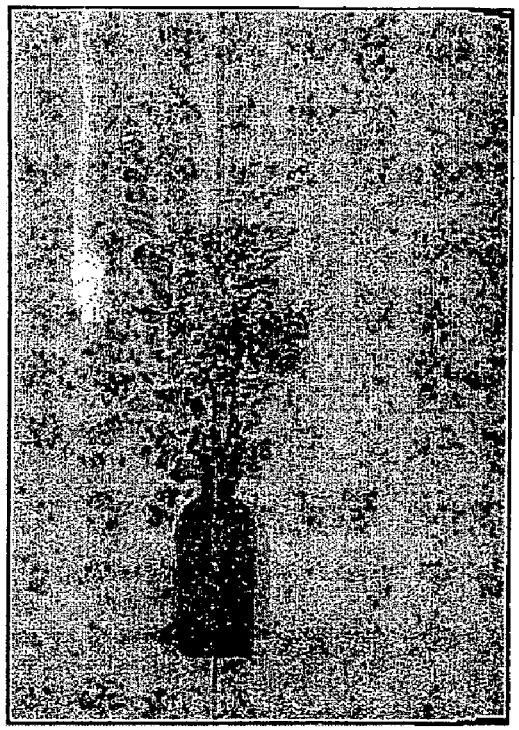
FIG. 37: Illustrates the unified crop boundaries for the set of images.
Figure 38:
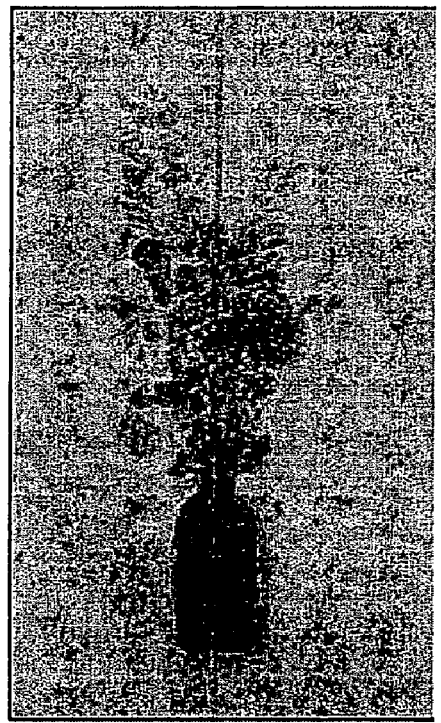
FIG. 38: Illustrates the final crop boundaries for the set images after balancing the left/right distance for the crop boundaries around the axis of rotation.

The next step is to find an inscribed rectangle in this polygon. An inscribed rectangle is illustrated in FIG. 35. They are a number of potential inscribed rectangles for any polygon, so one must be found which maximizes any one of a number of possible criteria. We may choose to maximize area, width, height, perimeter, or maximum symmetry to the virtual axis of symmetry, for example. In this case we choose to maximize area, as illustrated in FIG. 36. The entire sequence of images is cropped against this maximum area inscribed rectangle to yield a cropped rectified sequence as illustrated in FIG. 37. Finally, it is desirable to make the axis of symmetry centered in the entire sequence. This can be done by cropping the sequence again, such that the axis of symmetry is horizontally centered in the sequence, as illustrated in FIG. 38.

Determination of Center of Rotation

Figure 40:
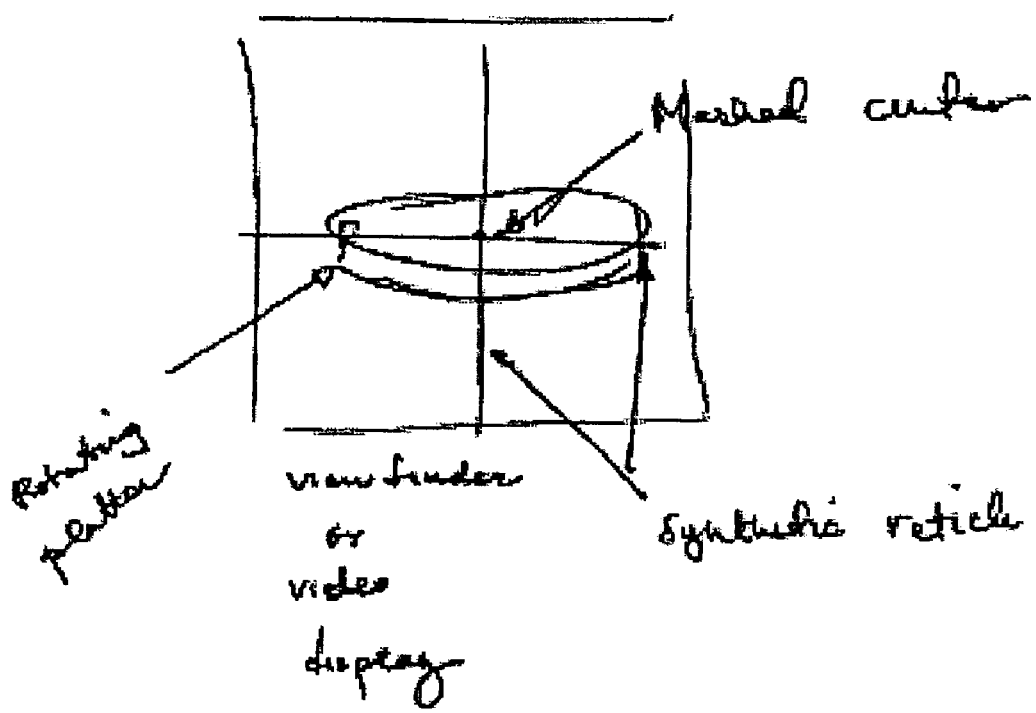
FIG. 40: Illustrates the synthetic reticle for the alignment of the rotating platform.

Alternatively, the center of the rotating platform may be marked and the video camera image can use a synthetic reticle down its center (vertical line which terminates at the visible center dot on the platform) to align the center of the platform with the center of the optic axis of the camera. This is illustrated in FIG. 40. The object can then be positioned using this synthetic reticle such that it rotates in a symmetric fashion in the image sequence.

Compression

One of the major problems to be overcome in order to make the use of omni-directional viewing technology is long download times for omni-directional view sequences when a limited connection speed to over a communications network such as the Internet is used. In order for consumers to avail themselves of the opportunity to browse and interact with product using omni-views, a parsimonious and highly compressed description of the views is highly desirable. It is also necessary that whatever compression technology is used maintains the image quality while decreasing the amount of time that it takes to download the object. We describe a view sequence compression designed for a set of omni-directional views that achieves compression by using redundant visual information overlap from neighboring omni-directional views.

Figure 41:
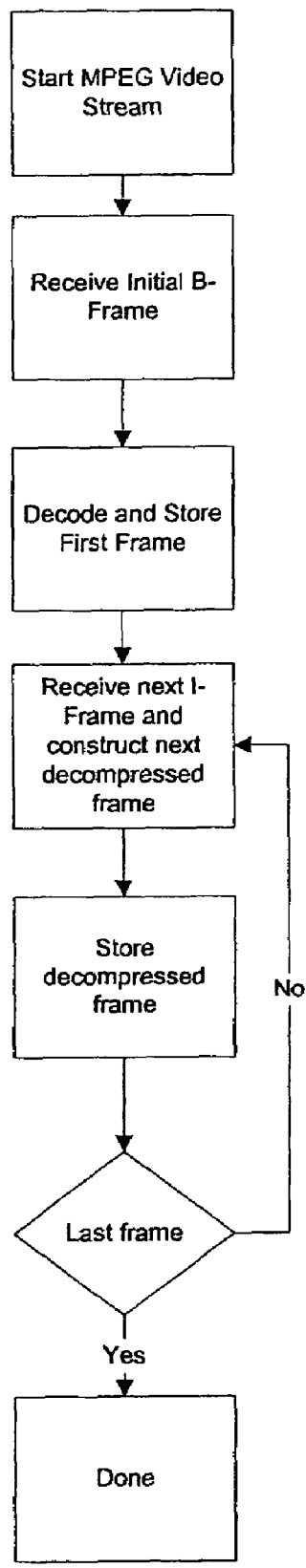
FIG. 41: Illustrates the video decompression sequence for receipt and storage of the multimedia frame.

If only small changes in the actuators occur from frame to frame in the set of omni-directional views that are sampled, a large amount of shared information may be present in the adjoining views. This sequence of adjoining view digital images may be treated as a digital video sequence and compressed using any one of a number of existing digital video compression techniques and standards, such as MPEG-1, MPEG-2 or newer standards such as MPEG-4. The system differs from these existing approaches in the file is not encoded using a minimum of B frames. This can be achieved since there are no large discontinuities since the object is sampled from adjoining points in the view sphere. However, rather than treat the video sequence as real-time stream, the compressed sequence can be downloaded, the image sequence decompressed and reconstructed by a CODEC on the client. Once the original image sequence has been reconstructed the image sequence can be cached on the browser client and interactively controlled. This process is illustrated in FIG. 41.

Furthermore, hyper-compression may be achieved by allowing the client to interpolate between key-stored views using any one of a number of techniques for image space morphing. In this case, the key views and morphing parameters are transmitted to the media player, which then can dynamically, render, or pre-render intermediate views and store them for fast viewing.

Figure 42:
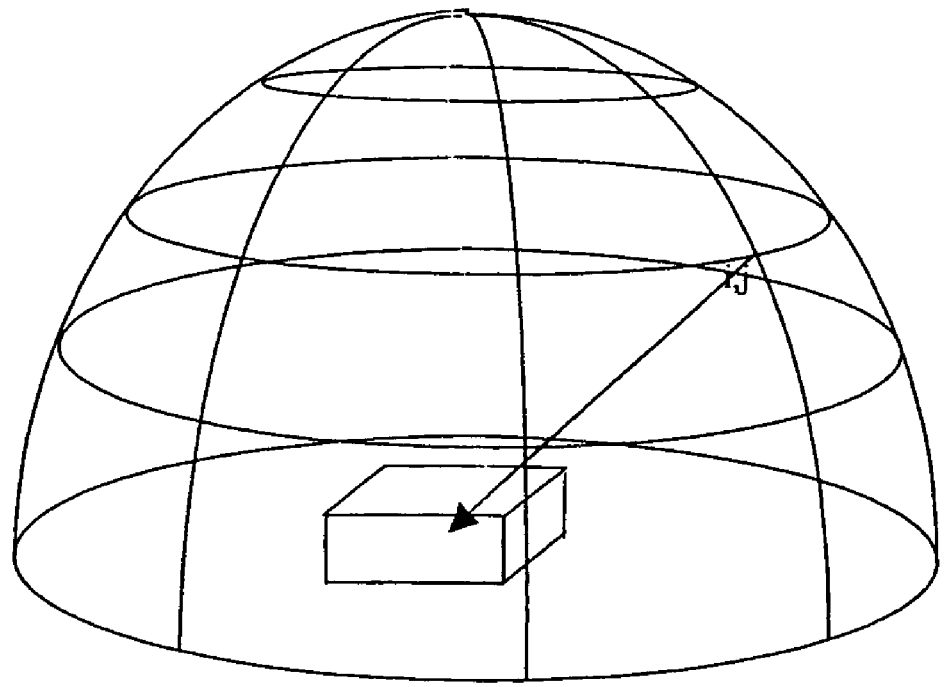
FIG. 42: Illustrates Spherical Coordinate Scan Pattern for object image acquisition.
Figure 43:
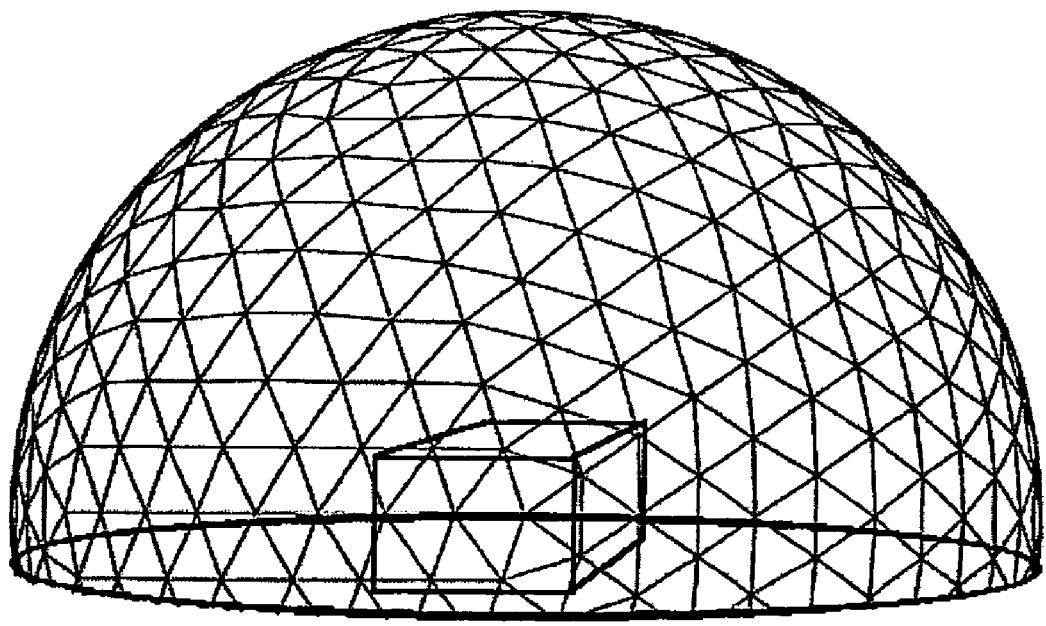
FIG. 43: Illustrates Geodesic Scan Pattern for object image acquisition.

This sequence of images which tile the view sphere can be indexed using a number of different tessellations of the viewsphere. For example a Geodesic tessellation or Cartesian tessellation may be employed as illustrated in FIG. 42 and FIG. 43. Each point on the tessellation can be linked to its nearest neighbor view points, both in azimuth and elevation as well as zoom. By using on screen controls to allow the user to traverse this tessellation and thus the sequence of views the user may be given the impression of interactively rotating the object around in three-dimensions and zooming in and out.

Exploitation of Human Motion Perception System Characteristics

Enhancements to the above system are possible to achieve even better compression at the expense of some viewpoint flexibility for the user. The perceptual capabilities of the human visual system are such that the spatial resolution for dynamic moving scenes is much less than that of a static scene. This non-uniformity of resolution can be exploited by using lower resolution sequences when the object is being dynamically rotated by the user and then selected a key frame (which has a key view) and is encoded at a higher resolution when the slider bar is released by the user as illustrated in FIG. 17. This allows the users to more closely inspect the detail of the object in key views. Additionally, these key views may be encoded in a pyramid representation. Thus when the viewer applet detects that the slider bar is not moving for more than a given timeout, the system downloads progressively higher resolution incremental pyramid representation layers for the given view. This pyramid representation can also allows for dynamic zooming into areas of the object for closer inspection.

View Sphere Encodings

Figure 44:
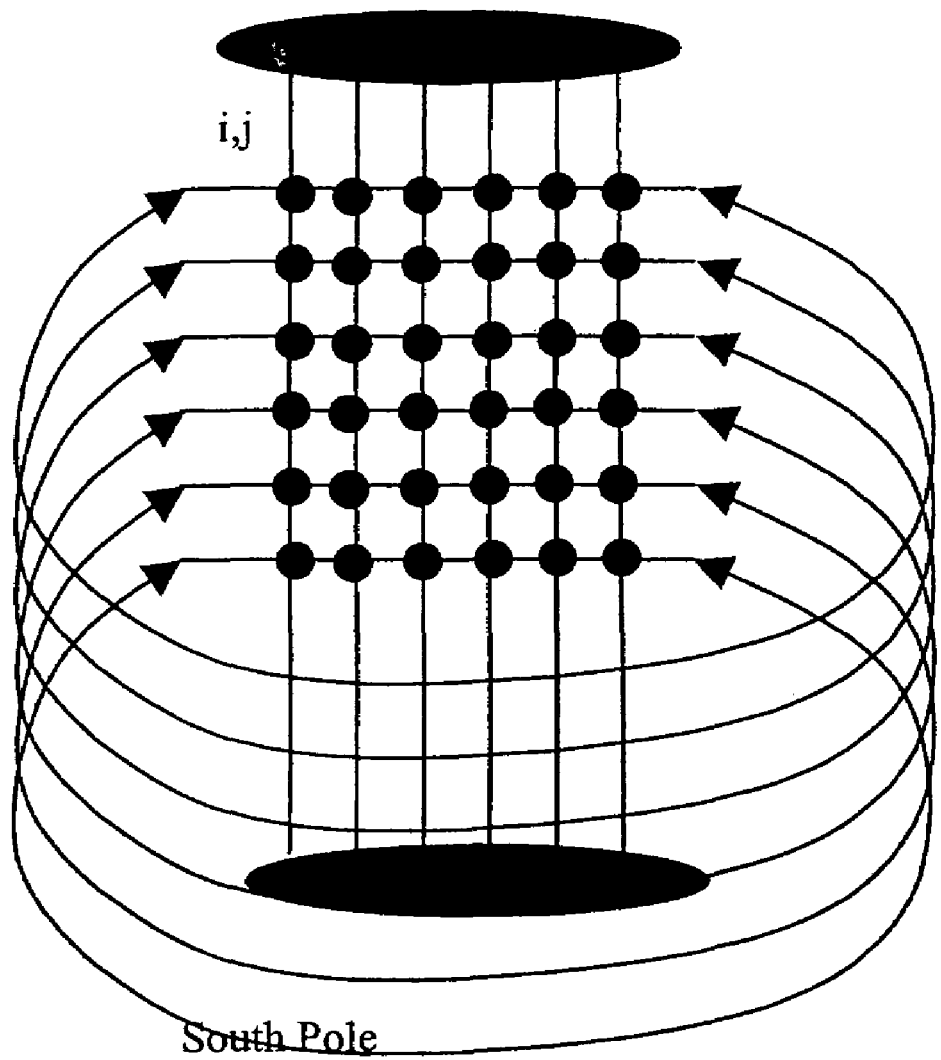
FIG. 44: Illustrates the Spherical View Indexing Torus.
Figure 45:
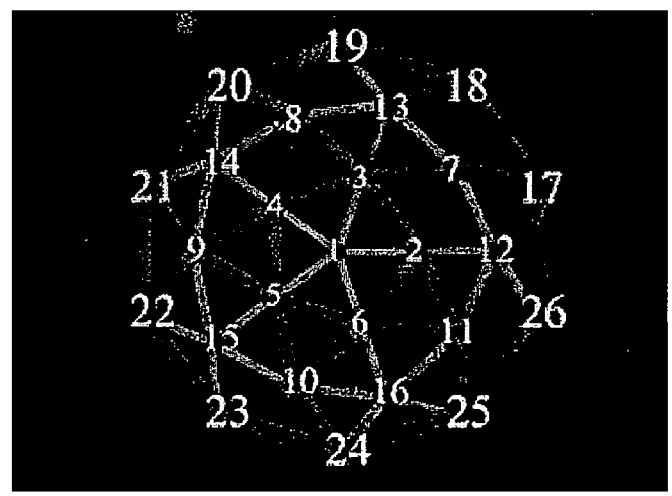
FIG. 45: Illustrates the Vertex indices for Geodesic Dome—Frequency 2—Class 1 (Top View of Hemisphere).

The sampling of the view sphere surrounding the object can be done using a variety of regular constructions including a spherical coordinate grid mapping (See FIG. 42) or a Geodesic or other uniform tiling of the sphere (See FIG. 43). These grid mappings on the sphere are known as the view sphere. The spherical coordinate grid mapping can be unfolded and flattened into a view torus and each view indexed by an azimuth and elevation index i,j (See FIG. 44) or a vertex index (see FIG. 45) The i,j th index indexes to the image acquired at the set of actuator values which correspond to a camera view and optic axis of the camera to pointing the origin of the sphere with the camera focal point at a given location on the surface of the view sphere as illustrated in FIG. 42.

In the case of the spherical mapping, it is desirable the ordering of the views in the file sequence be ordered such that progressive downloading of views is possible. For example, rotational views taken every 90 degress can first be downloaded in a breadth first fashion, followed by the interposed 45 degree views, and the 27.5 degree views etc. This allows for a coarsely quantized (e.g. every 90 degrees) 360 degree view set to be available rapidly and viewable before all intermediate views are downloaded and rendered by the viewer.

The advantage of the Geodesic triangulation is that it is a uniforming tiling of the sphere, which means the change in view is uniform for any change in view index for neighboring view point, independent of current view location, which is not the case with a latitude, longitude spherical coordinate tiling, and allows a good approximation to a great circle trajectory between any two points for smoother panning. This allows a more uniform views experience an predictable view change for trajectories along the view sphere as compared to a simple Cartesian spherical or cylindrical coordinate mapping.

Each index in the above representations can be augmented with a third index which represents a zoom factor which is equivalent to an effective optical absolute distance of the camera to the object that is achieved by varying the focal length of the zoom lense. Thus a set of "view shells" of view spheres can be indexed by a third index which specifies the shell being selected.

Additionally, each location can be augmented with camera pitch and yaw offsets, which can be integer or angular which allow for particular offsets that allow the camera to fixate on portions of the object not centered at the origin of the sphere.

Progressive Downloading

The sequence of images in the multimedia object sequence M can be of progressively higher resolution. It is convenient to use the Gaussian Pyramid Representation. Assume the N image are taking in rotational sequence around the object with resolution $2^m$ by $2^m$ pixels. As m increases by 1, the size of the image in pixels quadruples. Therefore it is desirable to first download the low possible resolution (m small, e.g. 6) then gradually increase m and download the higher resolution pyramid coefficients and re-render the image, showing progressively more detail. The first sequence can be displayed interactively and the images updated in the background and swapped in as they finer detail images arrive. Since motion vision has lower spatial resolution than static vision in humans, the viewer will be able to understand the 3D structure initially and then as further details is desired at later temporal moments, the higher resolution images will become available. This description is not meant to rule out other progressive downloading techniques such as those enabled by multi-scale wavelet or fractal encodings.

Miscellaneous

Enhanced Registration Between on-Line and Self-Contained Kiosk (Public Access)

Each item to be acquired must be entered and indexed into a database in the Storage and Caching Server indicated in FIG. 2 in a registration step. Normally the user connects enters information regarding the index and object specific descriptive information through the Host Application Server indicated in FIG. 2. The user may need to enter descriptive textual information regarding the type, quality, features and condition of the object, which can take some time to type in. In the embodiment for the Self-Contained Kiosk located in a public location, it is desirable to avoid the carrying out of this registration at the Self-contained scanner, since it could be a time-consuming process and could lead to slow throughput and underutilization of the scanner. Because it may take a significant amount of time to register a given object by a user, it is desirable to carry out the registration process on another PC. This permits the user to take as much time as they need, without time pressure to carry out the registration of the item. Once this registration is complete, the user may utilize the public access scanner solely for image acquisition, thus maximizing the availability of the system. However, registration of the item in one location and photography in another leads to the need to link the particular database entry to the image sequence to be acquired. Each view sequence must be uniquely identified. As a database of view sequences grows larger, the each identifier for a database record correspondence to a view sequence must grow longer to maintain uniqueness as a primary database key (See FIG. 18). Unfortunately such long identifiers may be cumbersome to remember by users and to key in to the system by the person desiring to scan a new object in to the system. In particular, the unique identifier may correspond to uniform resource locator which specifies the location on the internet where the view sequence is located and may be viewed or linked. With long sequence number and URL, the possibility that the user will mis-type or forget the index increases. We describe a process which decreases this possibility and simplifies the process for the user.

In our system, it useful to facilitate the use of such a scanning system in linking the objects to a Uniform Resource Locator URL, by use of a bar-code which encodes the a unique identifying alphanumeric sequence which will link to the published scan location URL.

Figure 46:
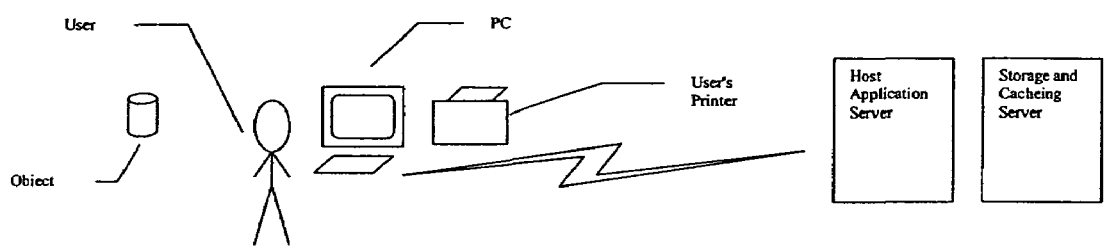
FIG. 46: Illustrates the Registration of Unique Item Number: using Print on Demand Bar-Code
Figure 47:
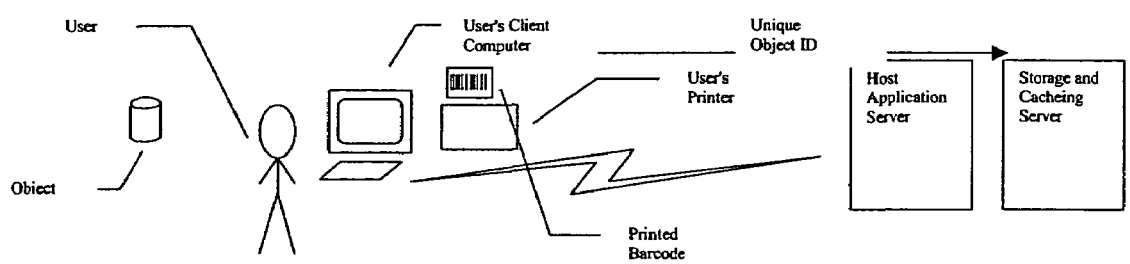
FIG. 47: Illustrates the On-Demand Printing of Unique Bar Code ID using Printer at User's PC.
Figure 48:
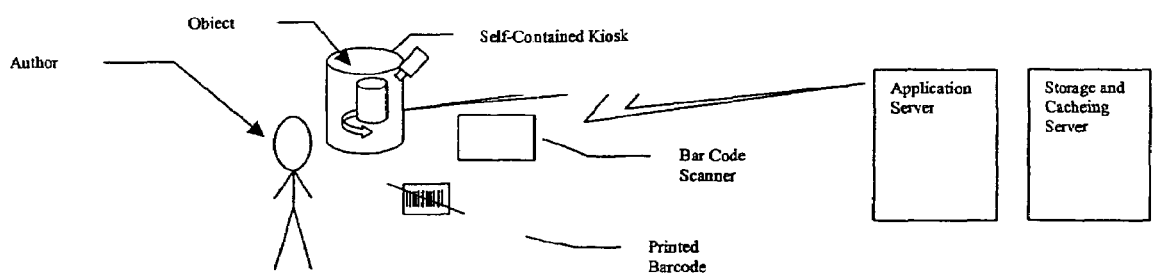
FIG. 48: Illustrates the Point of Scan Key-board Correspondence of Item with Printed Bar Code and Acquisition, Encapsulation and Publishing of Item.
Figure 49:
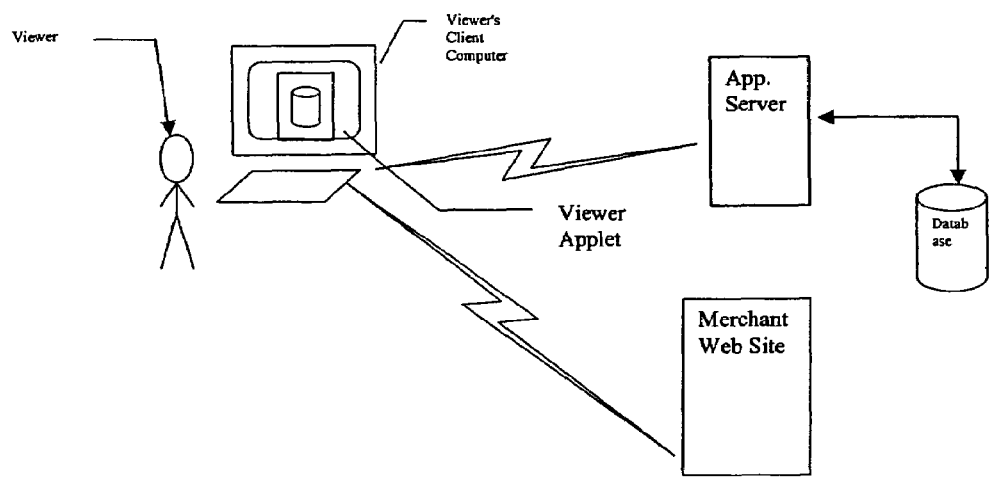
FIG. 49: Illustrate the Hyperlinking to View Hosting Service.

As FIG. 46 illustrates, using a subset of the elements indicated in FIG. 2, an individual that desires perform image acquisition an object can connect to the application server via a communications link (such as the Internet). The individual can connect to the scan-service's Host Application Server and request a new unique identifier for an object. Optionally, the user may enter a textual description and title for the object to be scanned. After this information is entered, a process at the Host Application Server's site generates a digital representation of the bar-code which encodes the unique object identifier and sends that representation to the user's computer. They user may then print out the bar code using the user's printer hooked to the user's client computer to print out the bar-code as illustrated in FIG. 7.

This printed bar-code is then brought to the publicly situated scanning kiosk and scanned by a bar-code scanner which is part of the scanning kiosk as illustrated in FIG. 8. In FIG. 8, the user has brought the object corresponding to the bar-code along with the printed bar-code to a location, such as a retail point of sale location in a copy center (e.g. Kinko's). The user places the object in the Object View Acquisition Kiosk. The printed bar-code is scanned and then the view acquisition is activated. The kiosk acquires, compresses and formats the view sequence file and sends it over the communications link to the Application server, which stores the sequence in the view sequence database using the scanned unique object identifier as its retrieval key. The user may review the quality of the view sequence using the preview display available on the kiosk scanner before finalizing the view sequence in the database.

By using this approach, no typing is needed at the kiosk, since the data entry can be carried out at another location, such as in the user's home, using their home PC. This, increased the speed at which items can be scanned, and maximizes the utilization of the machine, decreasing the wait when a queue forms at the machine. Additionally, since the user need not key in information at the kiosk, there is nothing for them to mis-key at the kiosk—data entry can be done at the leisure of the user on their home PC—they only need bring the printed out bar code corresponding to the item they are going to scan. This decreases the amount of time that the user must spend at the public scanner, which maximizes the availability and through put of the scanner.

Flash or other Formats

The use of Java based multimedia programs as an example in this document is not meant to restrict the use of these techniques, other multimedia program formats such as Macromedia Flash Scripts or equivalent may be used.

Additional Multimedia Capability

Other types of dynamic multimedia image presentations that may be generated using the above processes include rollover or hot spot based zoom where a magnified image of a region may be activated by clicking in a highlighted zone in the image to reveal further detail about the object, as well as additional textual information.

The same sequential image selection techniques may be used to animate the function of objects, rather than to animate the rotation of objects through the sequence of a set of images when step through the articulation of a given object.

This is not meant to restrict the type of multimedia techniques which may be achieved with the herein mentioned processes and architecture.

Tracking of Utilization of Applets in Email

With the addition of a unique ID (such as a GUID or UUID) embedded in each generated applet, described notationally as A(k,ID) in the encapsulated set {A(k,ID),E(K),S}, a system for the tracking of the utilization and effectiveness of the applet when embedded in a multimedia email may be accomplished. Each time the applet is executed on a client (a "view") its unique ID can be sent back to a tracking server which an correspond the Unique ID with the identity of a user that was sent the message, or a pseudonym which persistently links a user ID to a person while maintaining stronger confidentiality. If total anonymity is required by the respondents, the total number of applet views may be tabulated to gauge the effectiveness and response rate of the media campaign.

In the formation of a mailing list, a table of correspondence between the ID and the email recipient address may be formed which is used to track the utilization and forwarding of the applet. In particular, the applet may connect back with a particular tracking server whenever the applet is activated and report the duration of viewing as well as any interactive events and durations which can be used to monitor the effectiveness of a given multimedia presentation. In particular, http links may be embedded in the multimedia sequence and when activated, the selection of the particular events can be reported to the tracking server to tabulate the overall response and escalation of interest of the particular viewing event. Secondly, by uniquely keying each applet, the tracking of forwarded emails is also possible, which can also be used to grade the effectiveness of a given campaign.

One Click View Linking

A view sequence enablement button may be added to a page in the merchant or auction web-site which describes the item for sale. By having an authenticated and authorized user click that enablement button, a process executes on store front web site which lists the available view sequences that are currently hosted and available to that user. The user can select the appropriate view sequence. The process on the merchant's web site responds by adding the appropriate commands to the page which links the view sequence and embeds it into the page automatically. This process is termed "one-click view linking."

This "one click view linking" may be implemented in the following manner. The "click to link" button is a hyperlink to a given URL which is parameterized by the subscribers name. The URL which is dynamically created from the image database, contains a list of thumbnails for the given subscriber, as stored by the image sequence database. Each of the thumbnails is a hyperlink to a dynamically created hyperlink which embeds the referring page name as a parameter. By clicking the hyperlink, a CGI script is instantiated which causes the subscriber host to establish a connection message which indicates the referring page which is to be updated with the URL of the desired sequence. The Target updates the link and acknowledges. After this acknowledgement, the current page is auto-referred back to the original page having the one-click button.

Javascript Media Viewing Implementation

Figure 50:
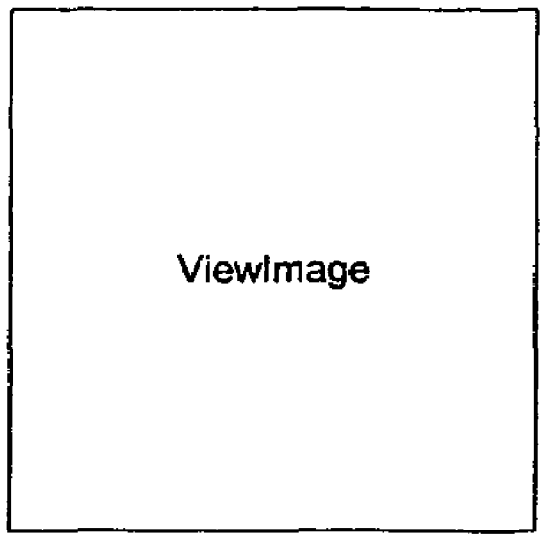
FIG. 50: Illustrates the document object layout for the Javascript media sequence presentation.
Figure 50:
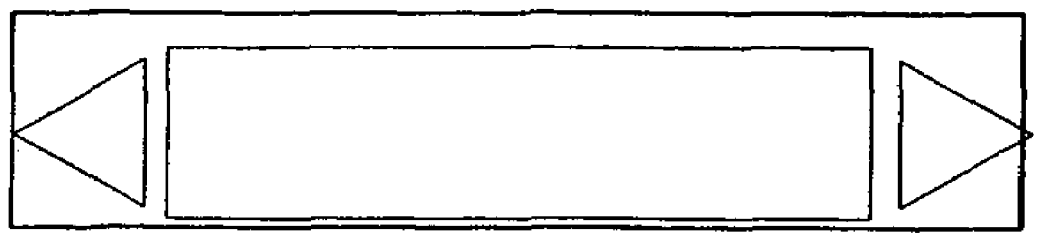
Figure 51:
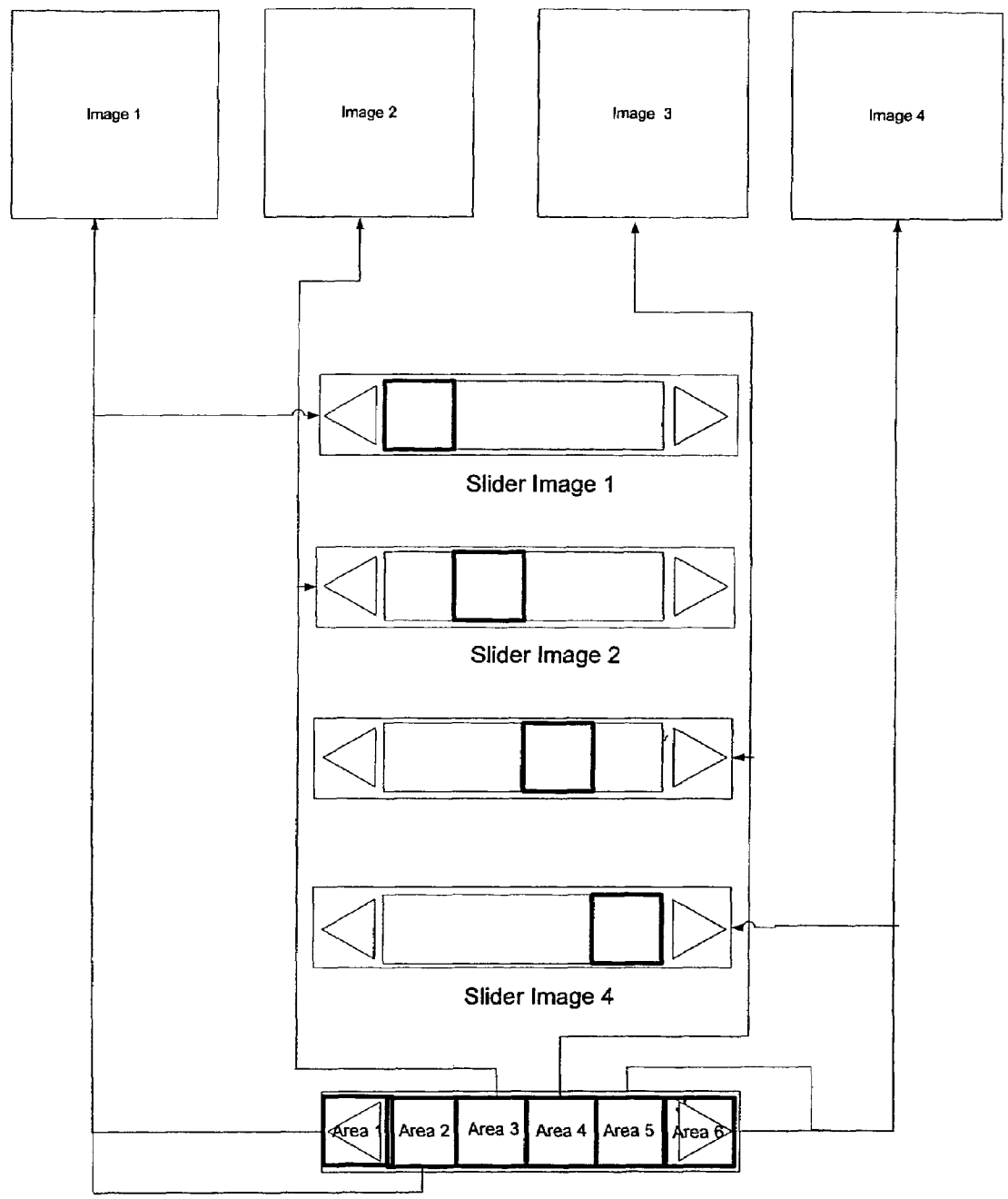
FIG. 51: Illustrates the images dynamically loaded when corresponding sections of the slider image map a selected via mouse.

It may desirable to using a Javascript program on the Web Browser client to render the multimedia sequence instead of using a Java applet due to the fact that certain browsers may not support the Java language, or may have the language disabled as a result of the browser's configuration options. Normally, it is not possible to have a "slider" Graphical user interface component controlling screen state without Java or ActiveX extensions to a browser. The following approach allows the simulation of a slider component. FIG. 50 illustrates a web page layout with 2 image document objects within a web browser, the View Image, which is used to render a particular image representing a particular view of the object, and the slider image, which is used to dynamically present the state of the slider control. A slider control may be simulated by pre-rendering of the slider in all possible positions, along with the set of View images, which is illustrated in FIG. 51. A Javascript program embedded in the HTML code for a web page may be used to establish an image map which breaks the slider image into a set of areas. When the user's mouse is passed over each respective image map area, the appropriate view and slider images are dynamically loaded into their respective document objects, replacing the currently rendered images. As this occurs dynamically, the effect is to animate smoothly the changing slider bar, and corresponding object views. A representative activation sequence is illustrated in FIG. 51 where the arrows from image map area point to the particular images that are loaded into the View Image Document object locations, and Slider Image Document object locations respectively. While this figure illustrates this for 4 potential slider locations and corresponding views, the approaches may be generalized for an arbitrary number of views by splitting the slider object into a set of image map areas which evenly divide the image area width for the slider, and load the corresponding view image for that slider image area. FIG. 52 is a listing of Javascript source code which implements the diagram depicted in FIG. 51.

It is understood, therefore, that the present invention is susceptible to many different variations and combinations and is not limited to the specific embodiments shown in this application. The terms "server", "computer", "computer system" or "system" as used herein should be broadly construed to include any device capable of receiving, transmitting and/or using information, including, without limitation, a processor, microprocessor or similar device, a personal computer such as a laptop, palm, PC, desktop or workstation, a network server, a mainframe, and an electronic wired or wireless device. Further, a server, computer, computer system, or system of the invention may operate in communication with other systems over any type of network, such as, for example, the Internet, an intranet, or an extranet, or may operate as a stand-alone system. In addition, it should be understood that each of the elements discloses all do not need to be provided in a single embodiment, but rather can be provided in any desired combination of elements where desired. It will also be appreciated that a system in accordance with the invention can be constructed in whole or in part from special purpose hardware or from conventional general purpose hardware or any combination thereof, any portion of which may be controlled by a suitable program. Any program may in whole or in part be comprised of or be stored on a system in a conventional manner, or remain whole or in part be provided into the system over a network or other mechanism for transferring information in a conventional manner. Accordingly, it is understood that the above description of the present invention is susceptible to considerable modifications, changes, and adaptations by those skilled in the art and that such modifications, changes and adaptations are intended to be considered within the scope of the present invention, which is set forth by the appended claims.

The invention claimed is:

1. An image processing method for identifying figure and background for the purpose of matteing and compositing, wherein two images are input, one with a foreground object and the other without, and the background areas are taken under similar scene illumination, the method comprising the steps of:
   computing the per pixel gray level absolute difference in intensity or vector color magnitude image difference between corresponding pixels in the two images;
   selecting those pixels locations which are above a relatively small threshold in terms of gray level difference or vector color magnitude difference to form a mask which selects only foreground object pixels locations.

2. The method of claim 1, wherein the masks are combined via a logical "OR" operation to generate a combined foreground object selection mask.

3. The method of claim 1, wherein features are identified and corresponded between two frames and affine transform components are used to align the two frames.

4. The method of claim 1, wherein an alignment wizard consisting of rotational, translation and scaling visual displays and GUIs are used to guide and assist a user in rectifying a media sequence of individual captured images.

5. The method of claim 4, wherein the media sequence is further processed to automatically crop for a maximum inscribed rectangle in the sequence, and the maximum inscribed rectangle is further centered around an indicated axis of symmetry for an object of interest.

6. The method of claim 1, wherein a unique database primary key corresponding to an object to be acquired is generated on a home personal computer, a bar coded encoding of the unique database primary key is printed on the home personal computer, the print out is brought to a self-contained view acquisition unit vending system and the bar code scanned, to avoid the re-keying of that unique database primary key.

7. An image editing method for identifying figure and background for the purpose of matting and compositing an object having a visual pattern or texture, which is placed on a textureless rotating platform in front of a fixed camera, and the background of the object is stationary and two or more images are captured, the method comprising the steps of:
   computing optical flow or time derivative for each pixel of each image in the image sequence, for yielding a flow vector having a magnitude and direction for each pixel;
   computing a magnitude for each pixel if the optical flow measure is used;
   threshold and label each pixel in the flow field with flow vector magnitude greater than threshold $\Theta$; and
   selecting pixels which are above a relatively small threshold in terms of optical flow magnitude, to form a mask which selects only foreground object pixels.

8. The method of claim 7, wherein the masks are combined via a logical "OR" operation to generate a combined foreground object selection mask.

9. The method of claim 7, wherein features are identified and corresponded between two frames and affine transform components are used to align the two frames.

10. The method of claim 7, wherein an alignment wizard consisting of rotational, translation and scaling visual displays and GUIs are used to guide and assist a user in rectifying a media sequence of individual captured images.

11. The method of claim 10, wherein the media sequence is further processed to automatically crop for a maximum inscribed rectangle in the sequence, and the maximum inscribed rectangle is further centered around an indicated axis of symmetry for an object of interest.

12. The method of claim 7, wherein a unique database primary key corresponding to an object to be acquired is generated on a home personal computer, a bar coded encoding of the unique database primary key is printed on the home personal computer, the print out is brought to a self-contained view acquisition unit vending system and the bar code scanned, to avoid the re-keying of that unique database primary key.

* * * * *